(12) United States Patent
Mancebo Molina et al.

(10) Patent No.: US 9,333,221 B2
(45) Date of Patent: May 10, 2016

(54) FAT BINDER OBTAINED FROM BIOMASS RESULTING FROM BEER PRODUCTION

(71) Applicants: Remedios Mancebo Molina, Barcelona (ES); Francesc Xavier Castañé Sitjas, Barcelona (ES); Jordi Cuñé Castellana, Barcelona (ES); Jonatan Santas Gutiérrez, Barcelona (ES); Magdalena Rafecas Martínez, Barcelona (ES); María Ángeles Beatriz Miralles Buraglia, Madrid (ES); Inmaculada Mateos-Aparicio Cediel, Madrid (ES); Ángeles María Heras Caballero, Madrid (ES)

(72) Inventors: Remedios Mancebo Molina, Barcelona (ES); Francesc Xavier Castañé Sitjas, Barcelona (ES); Jordi Cuñé Castellana, Barcelona (ES); Jonatan Santas Gutiérrez, Barcelona (ES); Magdalena Rafecas Martínez, Barcelona (ES); María Ángeles Beatriz Miralles Buraglia, Madrid (ES); Inmaculada Mateos-Aparicio Cediel, Madrid (ES); Ángeles María Heras Caballero, Madrid (ES)

(73) Assignee: S.A. DAMM, Barcelona (ES)

( * ) Notice: Subject to any disclaimer, the term of this patent is extended or adjusted under 35 U.S.C. 154(b) by 0 days.

(21) Appl. No.: 14/410,431

(22) PCT Filed: Jun. 21, 2013

(86) PCT No.: PCT/ES2013/070408
§ 371 (c)(1),
(2) Date: Dec. 22, 2014

(87) PCT Pub. No.: WO2014/001589
PCT Pub. Date: Jan. 3, 2014

(65) Prior Publication Data
US 2015/0174152 A1    Jun. 25, 2015

Related U.S. Application Data

(60) Provisional application No. 61/683,085, filed on Aug. 14, 2012.

(30) Foreign Application Priority Data

Jun. 25, 2012 (EP) .................................... 12382250

(51) Int. Cl.
| | | |
|---|---|---|
| A61K 31/722 | (2006.01) |
| A23L 1/30 | (2006.01) |
| A61K 36/064 | (2006.01) |
| C08B 37/00 | (2006.01) |
| C08B 37/08 | (2006.01) |
| A61K 31/716 | (2006.01) |
| A61K 35/741 | (2015.01) |
| C12F 3/10 | (2006.01) |

(52) U.S. Cl.
CPC ............. *A61K 31/722* (2013.01); *A23L 1/3018* (2013.01); *A61K 31/716* (2013.01); *A61K 35/741* (2013.01); *A61K 36/064* (2013.01); *C08B 37/003* (2013.01); *C08B 37/0024* (2013.01); *C12F 3/10* (2013.01); *A23V 2002/00* (2013.01); *A23V 2200/00* (2013.01)

(58) Field of Classification Search
None
See application file for complete search history.

(56) References Cited

U.S. PATENT DOCUMENTS

| | | | |
|---|---|---|---|
| 4,810,646 | A | 3/1989 | Jamas et al. |
| 5,932,561 | A | 8/1999 | Meyers et al. |
| 6,333,399 | B1 | 12/2001 | Teslenko et al. |
| 2007/0299034 | A1 | 12/2007 | Versali et al. |

FOREIGN PATENT DOCUMENTS

| | | |
|---|---|---|
| EP | 1483299 B1 | 8/2006 |
| GB | 2026515 A | 2/1980 |
| WO | 9103495 A1 | 3/1991 |
| WO | 9625437 A1 | 8/1996 |
| WO | 9921566 A1 | 5/1999 |

OTHER PUBLICATIONS

Mhurchu, C. Ni, et al.; "Effect of chitosan on weight loss in overweight and obese individuals: a systematic review of randomized controlled trials," Obesity Reviews, 2005, pp. 35-42, vol. 6.
Brady, D., et al.; "Chemical and Enzymatic Extraction of Heavy Metal Binding Polymers from Isolated Cell Walls of *Saccharomyces cerevisiae*," Biotechnology and Bioengineering, 1994, pp. 297-302, vol. 44.
Bornet, A., et al.; "Chitosan, chitin-glucan and chitin effects on minerals (iron, lead, cadmium) and organic (ochratoxin A) contaminants in wines," Eur Food Res Technol, 2008, pp. 681-689, vol. 226.
Keser, Onur, et al.; "Effects of Chitosan Oligosaccharide and/or Beta-Glucan Supplementation to Diets Containing Organic Zinc on Performance and Some Blood Indices in Broilers," Pakistan Veterinary Journal, 2012, pp. 15-19, vol. 32.
Nwe, Nitar, et al.; "Production of Fungal Chitosan by Enzymatic Method and Applications in Plant Tissue Culture and Tissue Engineering: 11 Years of Our Progress, Present Situation and Future Prospects," Biopolymers, 2010, pp. 135-162, Chapter 7.
Yao, Hsein-Tsung, et al.; "Effect of Chitosan on Plasma Lipids, Hepatic lipids, and Fecal Bile Acid in Hamsters," Journal of Food and Drug Analysis, 2006, pp. 183-189, vol. 14.

(Continued)

*Primary Examiner* — Qiuwen Mi
(74) *Attorney, Agent, or Firm* — Tristan A. Fuierer; Moore & Van Allen, PLLC

(57) ABSTRACT

The present invention provides a polysaccharide rich composition comprising beta-glucan, chitin and chitosan, extracted from the cell wall of *Saccharomyces cerevisiae* from the by-product biomass resulting from a brewing process, the process for obtaining it and the uses thereof. The composition exerts, among other biofunctionalities, a selective fat binding effect so it is useful in the prevention and/or treatment of a disorder such as overweight, obesity, hypercholesterolemia, hypertriglyceridemia, blood hypertension and cardiovascular disorders. It can be formulated as edible, pharmaceutical or a veterinary product.

13 Claims, 3 Drawing Sheets

(56) References Cited

OTHER PUBLICATIONS

Gades, Matthew D., et al.; "Chitosan Supplementation and Fat Absorption in Men and Women," Journal of the American Dietetic Association, 2005, pp. 72-77, vol. 105.

Zhou, Kequan, et al.; "In vitro binding of bile acids and triglycerides by selected chitosan preparations and their physico-chemical properties," Food and Science Technology, 2006, pp. 1087-1092, vol. 39.
Database GNPD [Online]; Mintel; 2008, Anonymous: "Mushroom Chitosan," XP002682926, retrieved from www.gnpd.com; Database accession No. 964863.
International Search Report, Nov. 11, 2013.

FAT BINDER OBTAINED FROM BIOMASS RESULTING FROM BEER PRODUCTION

CROSS-REFERENCE TO RELATED APPLICATIONS

This application is filed under the provisions of 35 U.S.C. §371 and claims the priority of International Patent Application No. PCT/ES2013/070408 filed on 21 Jun. 2013 entitled "FAT BINDER OBTAINED FROM BIOMASS RESULTING FROM BEER PRODUCTION" in the name of Remedios MANCEBO MOLINA, et al., which claims priority to U.S. Provisional Patent Application No. 61/683,085 filed on 14 Aug. 2012 and European Patent Application No. 12382250.4 filed on 25 Jun. 2012, all of which are hereby incorporated by reference herein in their entirety.

The present invention relates to the fields of medicine and nutrition and particularly, to dietary supplements for use in weight control and in the reduction of cardiovascular negative fats.

BACKGROUND ART

Poor eating habits and lifestyle of our society have led to a growing public health problem. Within the current disintegration in reference to the recommended pyramid of daily food intake, the most critical points are found in excessive consumption of saturated fatty acids and cholesterol. 7% of saturated fatty acids in respect of the energy intake and <250 mg/day of cholesterol are recommended, while reality reaches values of 15% and 350 mg/day respectively. Excess in energy intake is mainly due to excessive consumption of saturated fats, while excessive intake of cholesterol is caused by to excessive consumption of animal products.

All epidemiological studies agree that the overindulgent consumption of fat-rich food concomitant with a decrease in energy expenditure by physical activity leads to a number of prevalent health disorders, overweight/obesity and hypercholesterolemia counted among the most serious ones. In addition to the impairment of the quality of life, overweight and obesity have been linked as causative factors with serious adverse health conditions that include cardiovascular diseases, type 2 diabetes, muscle-skeletal problems, and cancer. Hypercholesterolemia on the other hand, by leading to atherosclerosis, is believed to be a major risk factor for coronary heart diseases, the leading cause of death in developed countries.

In view of the above, non prescription lipid-lowering agents that could help to reduce body weight and lower cholesterol are being increasingly sought. As a result, irrespective of their varying and not always fully substantiated effectiveness, a multitude of over-the-counter lipid-lowering dietary supplements are being marketed. Among them chitosan, available in the form of capsules and tablets, is advertised to be able to both lower cholesterol and produce rapid weight loss.

Chitosan is a polyaminosaccharide derived from chitin. Chitin, one of the most plentiful renewable organic resources in nature, found mainly in the exoskeleton of crustaceans, is chemically a linear polymer composed of N-acetyl-D-glucosamine units and D-glucosamine units linked with β-(1-4)-glycosidic bond, wherein N-acetyl-D-glucosamine units are predominant in that polymer chain. The deacetylated form of chitin refers to chitosan. Chitin usually refers to a copolymer with a degree of acetylation of more than 40% [i.e., number of N-acetyl-D-glucosamine more than 40% and number of D-glucosamine less than 60%] and insoluble in dilute acids. The name chitosan is used for a copolymer with less than 40% DA [i.e., more than 60% DD (degree of deacetylation), number of N-acetyl-D-glucosamine less than 40% and number of D-glucosamine more than 60%] that, in most cases, will be soluble in dilute acid. Chitin and chitosan can be chemically considered to be analogues of cellulose in which hydroxyls at carbon-2 have been replaced by acetamido and amino groups, respectively. Chitosan possesses distinct chemical and biological properties attributable to the presence of multiple amino groups in its molecules. This can be exploited in a variety of processes, medical treatments included, and these are possible due to excellent biocompatibility and physiological inertness of chitosan.

Chitin and chitosan are found as supporting materials in many aquatic organisms (shells of shrimps and crabs and bone plates of squids and cuttlefishes), in many insects, in terrestrial crustaceans (*Armadillidium vulgare, Porcellio scaber*), in nematode, in mushrooms and in some of microorganisms (yeast, fungus and algae).

The aquatic shells contain approximately 30-40% protein, 30-50% calcium carbonate, and 20-30% chitin on a dry basis. These portions vary with crustacean species and seasons. Traditionally chitin is manufactured by the decalcification and deproteination of crab or shrimp shells, which involves the dissolution of calcium carbonate with acid solution and the removal of proteins in alkaline medium or with enzymes, respectively. Chitosan can then be obtained by deacetylating chitin with a hot alkali solution, and a decolorization step. This chitosan production process has a number of unfavorable characteristics. For example, the process requires expensive heat energy and caustic alkali, which is a potential health hazard. The process also produces large amounts of waste, thereby necessitating significant disposal costs. In addition, the supply of shrimp or crab shells is highly dependent upon seasonal and environmental factors, leading to unpredictable limitations on production capacity and to inconsistent physico-chemical characteristics in final products to be used for medical and agriculture applications. Moreover, chitosan from shells of shrimps can present antigens in the final product which could cause allergies to the consumer. Thus, although chitosan has been clinically well tolerated, it cannot be recommended to people allergic to crustaceans. These problems may be circumvented by extracting chitosan from different sources.

Nowadays research is focused on extracting pure chitosan from fungal cell wall components. To this aim, N. Nwe et al. studied the bond between chitosan and glucan in fungal cell wall to develop an enzymatic method for the production of very pure chitosan from fungus *Gongroella butleri* in a high yield (N. Nwe et al. 2010, "Production of fungal chitosan by enzymatic method and applications in plant tissue culture and tissue engineering: eleven years of our progress, present situation and future prospects" *Biopolymers*, edited by Magdy Elnashar, published: Sep. 28, 2010, chapter 7 pp. 135-162).

EP 1483299 describes a method that allows separating chitin from β-glucans in a controlled way without degradation or transformation of the chitin chains. The method is based on contacting fungal cells of *Aspergillus niger* with a basic solution, contacting the alkali-insoluble fraction with an acidic solution, whereby obtaining a suspension of acidified alkali-insoluble fraction comprising said cell wall derivatives, and finally contacting it with β-glucanase enzymes to obtain a chitin product or with a chitin deacetylase to obtain a chitosan product.

One application of chitosan is as a dietary antilipidemic supplement where, owing to limited hydrolysis by human digestive enzymes, chitosan passes along the digestive system up to the large intestine practically intact, acting effectively like a dietary fiber. Chitosan is thought to reduce fat absorption from gastrointestinal tract by binding with anionic carboxyl groups of fatty and bile acids, and interferes with emulsification of neutral lipids (i.e., cholesterol, other sterols) by binding them by hydrophobic bonds. The antihyperlipidemic potential of chitosan has been studied both in vivo and in vitro. In vivo studies include trials carried out both on animals and humans and consisted of a variety of determinations, mainly body weight, serum lipid levels, and lipid concentrations in feces. Remarkably, the data reported are conflicting. Although animal trials mostly showed reducing effects of chitosan on body weight and cholesterol levels (H. Yao et al., "Effect of chitosan on plasma lipids, hepatic lipids, and fecal bile acid in hamsters human trials failed to show these effects" *J. Food Drug Anal.* 2006, vol. 14, pp. 183-189), human trials failed to show these effects (M. D. Gades et al., "Chitosan supplementation and fat absorption in men and women" *J. Am. Diet. Assoc.* 2005, vol. 105, pp. 72-77, C. N. Mhurchu et al., "Effect of chitosan on weight loss in overweight and obese individuals: a systematic review of randomized controlled trials" *Obes. Rev.* 2005, vol. 6, pp. 35-42).

Chitosan supplement formulations are similar but not identical. Chitosan itself is the product of chemical deacetylation of the raw material chitin, and the degree of deacetylation in the product varies with reaction conditions. Some factors during processing such as the degree of deacetylation and molecular weight of the molecules, chitin/chitosan ratio, solubility, ionic strength, pH, particle size, and temperature affect the production of chitosan and its properties. One may expect the efficiency of chitosan to depend on their physicochemical properties. However, no correlation has been established between the binding capacity and the measured physicochemical properties of chitosan. This is indicated in a study, among others, which reported the bile acid-binding capacity, fat-binding ability, swelling capacity, deacetylation degree, and solution viscosity of 11 selected chitosan preparations (K. Zhou et al., "In vitro binding of bile acids and triglycerides by selected chitosan preparations and their physicochemical properties" *Food Science and Technology* 2006, vol. 39, pp. 1087-1092).

Chitosan-based supplements are sold as "oil" trappers" and "oil magnets". Advertising claims for some of these supplements may give consumers unrealistic expectations. While it is advertised to be able to both lower cholesterol and produce rapid weight loss, they can at the same time cause antinutritional effects due to their ability to trap also lipid-based molecules which are beneficial for human health, such as fat-soluble vitamins A, D, E, K, HDL cholesterol, vegetal sterols, and polyunsaturated fatty acids such as omega 3 and 6 fatty acids.

SUMMARY OF THE INVENTION

The present invention provides a polysaccharide rich composition comprising beta-glucan, chitin and chitosan, extracted from the cell wall of *Saccharomyces cerevisiae* from the by-product biomass resulting from a brewing process, the process for obtaining it and the uses thereof. As the composition of the invention is rich in polysaccharides (chitin, chitosan and beta-glucan) it is named in this description as "polysaccharide rich composition". "The composition", "the product" and "the composition of the invention" are also used indistinctively to refer to the composition of the invention.

Accordingly, a first aspect of the invention relates to a process to obtain a polysaccharide rich composition comprising beta-glucan, chitin and chitosan, extracted from the cell wall of *Saccharomyces cerevisiae* from the by-product biomass resulting from a brewing process, comprising the following steps:
i) preparing a reactor with a NaOH solution in a concentration between 0.25 and 3 M with agitation and a temperature between 50 and 95° C.;
ii) adding the biomass resulting from the brewing process to the solution;
iii) keeping the conditions during at least 1 hour;
iv) chilling the solution until room temperature,
v) neutralizing the solution by at least one addition of an acidic solution or of water, until reaching pH 7, wherein when more than one addition is made, an step of separation of the solid product from the solution is performed between additions;
vi) separating the solid product obtained in step (v) from the solution;
vii) when the neutralization in step (v) has been made by the addition of an acidic solution, submitting the solid product to at least one washing with water and separating the obtained solid product; and
viii) drying the solid product until constant weight and micronizing.

Another aspect of the invention is the provision of a composition obtainable by the process as defined above.

In exerting several beneficial effects in human, the composition of the invention is useful as a therapeutic or prophylactic agent. Thus, another aspect of the invention relates to the composition of the invention for use as a prevention and/or therapeutic agent. Particularly, the composition is useful in the prevention and/or treatment in an animal, including a human, of a disorder selected from the group consisting of overweight, obesity, hypercholesterolemia, hypertriglyceridemia, blood hypertension and cardiovascular disorders. The invention provides the use of the composition for the manufacture of a medicament for the prevention and/or treatment of the above mentioned disorders. This may be alternatively formulated as a method for the prevention and/or treatment of a disorder selected from the group consisting of overweight, obesity, hypercholesterolemia, hypertriglyceridemia, blood hypertension and cardiovascular disorders, in an animal, including a human, comprising administering to said animal in need thereof an effective amount of the composition of the invention.

Another aspect of the invention relates to the composition of the invention for use as a gut fat binder agent.

In another aspect the composition of the invention is useful as a detoxifying agent.

In another aspect, the composition of the invention is useful as a immunoestimulant agent.

Another aspect of the invention relates to a pharmaceutical and/or veterinary product comprising an effective amount of the composition as defined above, together with appropriate amounts of pharmaceutically or veterinary acceptable excipients. The term "effective amount" as used herein, means an amount of an active agent high enough to deliver the desired benefit, but low enough to avoid serious side effects within the scope of medical judgment.

A further aspect of the invention relates to an edible product comprising an effective amount of the composition of the invention, together with appropriate amounts of other edible ingredients.

DETAILED DESCRIPTION OF THE INVENTION

The cell wall of *Saccharomyces cerevisiae* may account for between 20 and 30% of the cell dry mass. It is mainly composed of mannoproteins and beta-glucans and smaller amounts of chitin and lipids. The proportion of these components may vary according to the strains and the culture conditions. As it has been described above, there are methods in the art to extract chitosan from fungal cell wall components. On the other hand, the art also discloses methods to obtain beta-glucans from yeasts, and particularly from *Saccharomyces cerevisiae*. WO 91/03495 discloses methods for producing soluble glucans to stimulate platelet production. One of the methods starts with whole glucan particles previously prepared from dried Baker's yeast according to the procedure of Jamas et al., U.S. Pat. No. 4,810,646, and comprises additional steps to solubilize the insoluble glucan particles. Another method described in Example 2 of the patent application relates to a sequence of treatments to produce soluble glucans from a selected strain of *S. cerevisiae*.

Thus, even though the art discloses methods to obtain on one hand chitin/chitosan and on the other hand beta-glucans from yeast, the quality and quantity of the final extracted product from the fungal mycelia depend on the fungal origin, their grow conditions (fermentation medium composition: carbon source and concentration, nitrogen source and concentration, and metal ions and their concentration; and fermentation conditions: inoculum size, harvesting time, fermentation temperature); and on the steps of the extraction process.

The invention provides an industrial process to obtain a polysaccharide rich composition. The process comprises the steps explained in the previous section. A reactor is prepared with a NaOH solution in a concentration between 0.25 and 3 M with agitation and a temperature between 50 and 95° C. In particular embodiments of the invention, NaOH concentration is selected from 0.25, 0.50, 0.75, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9 and 3 M. Particularly, NaOH is at a concentration between 0.25 and 1.5 M. More particularly, the concentration of NaOH is 0.25 M. In another particular embodiment, the concentration of NaOH is 1 M.

In another embodiment of the invention, the treatment with NaOH solution in the reactor is carried out at a temperature selected from 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, and 95° C. Particularly, temperature is between 65 and 85° C., and more particularly at 80° C.

In one embodiment of the invention, after chilling the solution (step (iv)), it is neutralized by the addition of an acidic solution to reach pH 7 and the solids are separated from the solution. Particularly, the acidic solution is a phosphoric acid solution, an HCl solution, or an acetic acid solution. Then, the solid product is submitted to at least one washing with water. Between washes, the solid product is separated from the solution.

In another embodiment of the invention, the step of neutralization is done by at least one addition of water, particularly distilled water. When more than one addition is made, a step of separation of the solid product from the solution is performed between additions. When the neutralization is made by additions of water, it would not be necessary to wash the solid after neutralization but it can be made if a cleaner solid product is desired.

In a particular embodiment of the invention, the process comprises a step before the neutralization, which consists in separating the solid product from the solution once chilled. Separation is for example made by centrifugation. In industrial scale-up, batch 2, for instance, has been done adding this step.

In a particular embodiment of the invention, the biomass resulting from the brewing process is added to the reactor in an amount between 1:2 and 1:5. Particularly the amount is 1:3. This is expressed as wet biomass:NaOH solution. As seen in the examples, batches 2-4 were made in this way adding amounts of biomass of 1:3 (batch 2 and 3) and 1:2 (batch 4). Expressed in dried product, the amounts used in said example would be 1:39 and 1:23 respectively.

Thus, the by-product biomass resulting from the brewing process can be added to the reactor with the NaOH solution directly coming from the brewing process. This biomass is therefore wet (herein referred as "wet biomass") because comprises impurities of the brewing process.

The by-product biomass resulting from the brewing process can also be added to the reactor dried. Therefore, in another embodiment, the process further comprises a pretreatment of the biomass resulting from the brewing process before adding the biomass to the NaOH solution. The pretreatment comprises the following steps: (a) sieving the biomass in order to separate the *Saccharomyces cerevisiae* biomass from impurities of the brewing process; (b) drying the *S. cerevisiae* biomass obtained in step (a); and (c) milling the *S. cerevisiae* product obtained in step (b). In this case, the addition of the dried *S. cerevisiae* product to the reactor is in an amount between 1:20 and 1:40 weight/volume. In particular the amount is 1:30 w/v. As seen in the examples, batch 1 was made in this way adding an amount of biomass of 1:30.

The conditions in the reactor are kept during at least 1 hour. Particularly, conditions are kept between 5 and 20 h and preferably, during 16 h. In another embodiment, the reaction takes 10 h (see for instance Batch 4).

The final product is dried and finally micronized. Preferably, the product is disposed in glass trays and dried in vacuum oven at 60° C. to constant weight, and then micronized. Drying can be performed under vacuum to reduce the process time. In a particular embodiment, drying is performed by spray-drying the product until a solvent content lower than 5% by weight.

The present invention covers all possible combinations of particular conditions described herein. The examples below (Batch 1-4) show that certain reaction conditions and process steps can be varied without significantly changing the product characteristics (as it can be seen in point 9.4 of the examples).

As a result of this process, a composition is obtained that comprises beta-glucan, chitin and chitosan, of the cell wall of *S. cerevisiae*. In an embodiment of the invention, the ratio of chitosan, chitin and beta-glucan in the composition is between 1:10:80 and 1:20:150. In another embodiment of the invention, the solubility of the composition at pH 3.5 in distilled water is between 650 and 800 mg/l. In another embodiment of the invention, the atomic mass percentage of carbon, hydrogen and nitrogen of the composition is respectively between 36 and 44% for carbon, between 5.5 and 7% for hydrogen, and between 0.2 and 0.8% for nitrogen.

In a particular embodiment of the invention, the process to obtain the composition is performed at a NaOH concentration of 0.25 M, at 80° C. with an amount of dried *S. cerevisiae* product in the reactor of 1:30 w/v, during 16 h of reaction time. Chemical properties of the composition obtained with these conditions are described in section 2 of EXAMPLES below. Particularly, the ratio of chitosan, chitin and beta-glucan in the composition is 1:14:116; the solubility of the composition at pH 3.5 in distilled water is 710 mg/l; and the atomic mass percentage of carbon, hydrogen and nitrogen of the composition is 40.32, 6.35 and 0.24%, respectively.

In a particular embodiment of the invention, the process to obtain the composition is performed at a NaOH concentration of 0.25 M, at 80° C. with an amount of *S. cerevisiae* wet biomass in the reactor of 1:3, during 16 h of reaction time. Before the neutralization step, the product is separated from the solution once chilled. In a particular embodiment, the product obtained has the properties described in section 9.4 Batch 2.

In a particular embodiment of the invention, the process to obtain the composition is performed at a NaOH concentration of 0.25 M, at 80° C. with an amount of *S. cerevisiae* wet biomass in the reactor of 1:3, during 16 h of reaction time. After hydrolysis, the mixture is directly neutralized by adding an acidic solution (without the first centrifugation of the reaction mixture). After neutralization, the mixture is centrifuged and then washed. In a particular embodiment, the product obtained has the properties described in section 9.4 Batch 3.

In a particular embodiment of the invention, the process to obtain the composition is performed at a NaOH concentration of 0.32 M, at 80° C. with an amount of *S. cerevisiae* wet biomass in the reactor of 1:2, during 10 h of reaction time. After hydrolysis, the mixture is directly neutralized by adding an acidic solution (without the first centrifugation of the reaction mixture). After neutralization, the mixture is centrifuged and then washed. In a particular embodiment, the product obtained has the properties described in section 9.4 Batch 4.

β-glucans are known as biological response modifiers because of their ability to activate the immune system. Furthermore, the European Food Safety Authority (EFSA) has concluded in a recent scientific opinion that a cause and effect relationship can be established between the consumption of beta-glucans and the reduction of blood cholesterol concentrations. The food constituent that was subject to study was beta-glucans which are soluble cereal fibers. Regarding weight control, none of the references presented to the EFSA addressed the effects of beta-glucan consumption on body weight so the panel concluded that a cause and effect relationship has not been established between the consumption of beta-glucans and the maintenance or achievement of a normal body weight (Scientific Opinion on the substantiation of health claims related to beta glucans and maintenance of normal blood cholesterol concentrations (ID 754, 755, 757, 801, 1465, 2934) and maintenance or achievement of a normal body weight (ID 820, 823) pursuant to Article 13(1) of Regulation (EC) No 1924/2006 EFSA Journal 2009; vol. 7(9) pp. 1254 [18 pp.]).

Surprisingly, the composition of the invention based on a mixture of beta-glucans and chitin/chitosan from *Saccharomyces cerevisiae* biomass from a brewing process has shown a lipid-specific lowering effect, as well as a weight reduction effect and a waist circumference reduction in human clinical trials.

The working examples below demonstrate that the composition of the invention involved a substantial improvement in the ability to improve the lipid profile of intakes. In a particular embodiment of the invention, the composition has a fat binding capacity of at least 10 times its weight, determined by an assay consisting of: i) contacting cotton oil with composition in an acidic solution during two hours at 37° C. and with constant agitation; ii) centrifuging the solution in order to separate the cotton oil bound to the composition from the non-bound cotton oil present in the supernatant; iii) mixing the supernatant with hexane and centrifuging the mixture; and iv) recovering the upper phase of the centrifuged mixture, allowing hexane to evaporate, and weighing the non-bound cotton oil. This assay is also explained in detail in section 3 of EXAMPLES.

The working examples below demonstrate also that animals fed with the product of the invention showed a less weight increase as compared to commercial similar fat binder products used as control groups. The energy efficiency (g of body weight gained per kcal of ingested feed) is the value which clearly shows product efficacy in reducing absorption. In this case, the product of the invention reduced total fat absorption measured as total feed efficiency, compared to controls. Consumption of the product of the invention did not imply a significant increase in fecal excretion in animals. The same cannot be said in the group of a commercial product (Chitosan S). Chitosan S product reached extraordinarily high values of excretion and dry matter. This fact, unlike what happens with the product of the invention implies that there is a non-selective effect in case of Chitosan S product, which would not specifically bind fat but many more nutrients. Thus the product of the invention has the advantage of lacking the anti-nutritional effects presented by other commercial fat binder products, as it is shown in the examples. The selective fat binding is of interest since the excretion of saturated fatty acids was significantly increased after DAMM product consumption. The product resulting from the process described in the EXAMPLE 1 is also named "DAMM product" or "Batch 1", hereinafter and throughout this document. That of monounsaturated fatty acids was increased, although results were not statistically significant, whereas that of polyunsaturated fatty acids did not increase.

The fat binding effect of the product of the invention has also been demonstrated in vivo in humans. The results of a functional clinical trial in humans showed a weight reduction of 0.7 kg and a decrease in waist circumference of 2 cm after treatment for 3 months. A reduction of 0.82% of total body fat was observed after taking the product. A redistribution of body fat reducing its accumulation in the abdominal area was observed. This is related to a potential benefit in reducing cardiovascular risk factors, hypertension and diabetes. With these results it can be inferred that the product promotes weight loss, with an overall reduction of 2.1 kg weight and a waist circumference reduction of 2 cm, taking into account that the placebo group in global showed an increase of 1.4 kg after 3 months of treatment. These results are clinically relevant since the results of decreased weight and waist circumference were obtained in the absence of specific restrictive diet and in a short time of treatment (3 months).

Besides the effect in reducing selectively the absorption of dietary fats, the composition of the invention also showed a biofunctionality in the metabolism of glucose. In oral glucose tolerance tests in an animal model, the blood glucose peak, particularly in time immediately postprandial, showed a reduction compared to negative control and the same order as the positive commercial control.

The product of the invention has also shown that it can be used as detoxifying agent since it captures different relevant toxics: the aflatoxin B1 mycotoxin, mercury, polychlorinated biphenyls (PCB 209) and furan.

Different replications of the process of obtaining the composition resulted in a homogeneous product which maintained the same mentioned biological functionalities. Thus, an advantage of the process and product of the invention is that the properties and usefulness of the final product do not depend on the raw material, as it happens with chitin/chitosan extracted from crustaceans. An additional and relevant advantage is that through the process of the invention identical material can be obtained throughout the year; and the extracted composition is free of heavy metal contents such as nickel, copper, which are present in compositions extracted from crustaceans.

In another embodiment, the process to obtain a polysaccharide rich composition comprises a second thermoalcaline treatment in order to modify the deacetylation degree of chitin. Thus, after neutralizing and separating the solid product obtained from the first reaction, the product is submitted to a second treatment with NaOH at a concentration between 25 and 50% at a temperature between 40 and 80° C. and with a reaction time between 30 and 240 minutes. Particularly, NaOH is at a concentration selected from 25%, 37.5% and 50%. Reaction temperature is selected between 40, 60 and 80° C.; and time is selected between 30, 120, 135 and 240 minutes. As it is shown in the working examples below (section 7), the products resulting from this treatment are useful as detoxifying agents since they are able to capture different relevant toxics: the aflatoxin B1 mycotoxin, mercury, polychlorinated biphenyls (PCB 209) and furan.

In another embodiment the fractions obtained from this second thermoalcaline treatment are useful as immunostimulant agents, as it is shown in the working example below (section 7). Specifically, in an in vivo study, the supplemented animals showed a greater protective capacity against bacterial infections, due to an increase in the percentage of activated cells with oxidative activity. A particular composition useful as immunostimulant agent is the one obtained by hydrolysis of the starting product for 30 minutes with 25% NaOH at 40° C. as obtained by the process explained in section 1 of EXAMPLES.

The invention also provides pharmaceutical and/or veterinary products that comprise an effective amount of the composition of the invention, together with adequate amounts of pharmaceutically or veterinary acceptable excipients. In this regard, the pharmaceutical product may be prepared to be administered orally in form of tablets, pills, capsules, microcapsules, granules, suspensions, syrups, dry powders, liquid preparations, etc. Selection of the excipients and the most appropriate methods for formulation in view of the particular purpose of the composition is within the scope of ordinary persons skilled in the art of pharmaceutical technology. Oral administration is preferred.

The term "pharmaceutically acceptable" as used herein pertains to compounds, materials, compositions, and/or dosage forms which are, within the scope of sound medical judgment, suitable for use in contact with the tissues of a subject (e.g. human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation. Suitable carriers, excipients, etc. can be found in standard pharmaceutical texts. Likewise, the term "veterinary acceptable" means suitable for use in contact with the tissues of a non-human animal.

The composition of the invention can be also included in a variety of edible products, such as a milk product, a yogurt, a curd, a cheese (e.g. quark, cream, processed, soft and hard), a fermented milk, a milk powder, a milk based fermented product, an ice-cream, a fermented cereal based product, a milk based powder, a beverage, a dressing, and a pet food. The term "edible product" is used herein in its broadest meaning, including any type of product, in any form of presentation, which can be ingested by an animal, but excluding pharmaceutical and veterinary products. Examples of other edible products are meat products (e.g. liver paste, frankfurter and salami sausages or meat spreads), chocolate spreads, fillings (e.g. truffle, cream) and frostings, chocolate, confectionery (e.g. caramel, fondants or toffee), baked goods (cakes, pastries), sauces and soups, fruit juices and coffee whiteners. Particularly interesting edible products are dietary supplements and infant formulas. In the sense of the present invention, dietary supplements also include nutraceuticals, which are known to be extracts of foods that have a medicinal effect on human health. Fodders for animal food are also included in the scope of the invention. The compositions of the invention could be also used as an ingredient in other food products. Accordingly, in another aspect of the invention, an edible product is provided which contains the composition of the invention together with appropriate amounts of edible ingredients. Preferably, the composition of the invention is a dietary supplement. If the composition according to the invention is used as a dietary supplement, it can be administered as such, or can be mixed with a suitable drinkable liquid, such as water, yoghurt, milk or fruit juice, or can be mixed with solid or liquid food. In this context the dietary supplement can be in the form of tablets, pills, capsules, granules, powders, suspensions, sachets, pastilles, sweets, bars, syrups and corresponding administration forms, usually in the form of a unit dose. Preferably, the composition of the invention is administered in the form of powder in a capsule or forming a pill, manufactured in conventional processes of preparing pharmaceutical products. In another preferred embodiment, the composition is presented in the form of powder within a bottle cap to be easily dissolved in a drinkable liquid. Suitable administration regimes of the composition of the invention can be established by the person skilled in the art. The composition of the invention can be administered once a day, once a week, several days per week or several times per day.

The composition according to the invention can be formulated as edible, pharmaceutical or veterinary product, in which the composition is the only active agent or is mixed with one or more other active agents and/or is mixed with pharmaceutically or veterinary acceptable excipients (in the case of a pharmaceutical or veterinary product) or adequate additives (in the case of an edible product).

Thus, it is understood that a subject may benefit from the functionalities of the product of the invention whichever is the form of administration, i.e. an edible, pharmaceutical or a veterinary product. The biological functionalities are those explained in this description and include the fat binding effects and their consequent use in the prevention and/or treatment of a disorder such as overweight, obesity, hypercholesterolemia, hypertriglyceridemia, blood hypertension and cardiovascular disorders. Biofunctionalities are also glucose binding effect, detoxifying effect and immunostimulant effect.

The following sections describe the process of obtaining the composition of the invention in detail, as well as the composition properties, including their fat binding effects through in vitro, and animal and human in vivo assays. The following examples and drawings are provided by way of illustration, and they are not intended to be limiting of the present invention. The results obtained demonstrate that the composition of the invention has improved features when compared with other fat binder commercial products.

Unless otherwise defined, all technical and scientific terms used herein have the same meaning as commonly understood by one of ordinary skilled in the art to which this invention belongs. Methods and materials similar or equivalent to those described herein can be used in the practice of the present invention. Throughout the description and claims the word "comprise" and its variations are not intended to exclude other technical features, additives, components, or steps. Additional objects, advantages and features of the invention will become apparent to those skilled in the art upon examination of the description or may be learned by practice of the invention. Furthermore, the present invention covers all possible combinations of particular and preferred embodiments described herein.

EXAMPLES

Example 1

Figure 1:
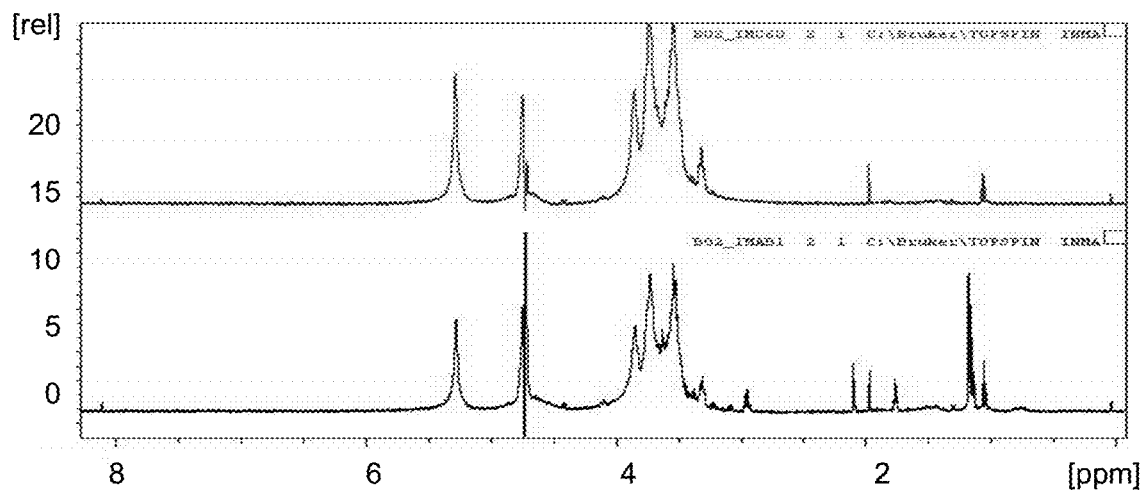
FIG. 1 shows the $^1$H-NMR analysis of DAMM product (lower figure) compared to the product obtained previously at laboratory scale (C60, upper figure).

Process to Obtain the Polysaccharide Rich Composition ("DAMM Product")

The *Saccharomyces cerevisiae* source to use as starting material derived from eight repeated uses in the brewing process. The brewing process by-product was sieved with a sieve of 1 mm in order to separate the *S. cerevisiae* biomass from impurities of the brewing process. The *S. cerevisiae* biomass obtained was dried in a heater and milled to obtain a powder.

Humidity of the yeast biomass was determined with a humidity analyzer IR Sartorius MA30. The reaction medium was prepared loading the reactor with distilled water, adjusting the stirring at 150 rpm, adding the amount of NaOH needed to obtain a NaOH solution 1 M and then heating the reaction medium at 80° C. Yeast biomass was weighed to a ratio of dry yeast biomass/reaction medium volume of 1/30. The yeast biomass was added to the hot reaction medium, and the reaction was maintained for 16 h. Once the reaction time elapsed, the product was chilled until room temperature. Subsequently, the reaction volume was downloaded to an inert container. The operating conditions of continuous centrifugation were adjusted to 120 seconds of spin time, and 2 seconds of downloading (discharge) time. Centrifugation was done feeding the centrifuge (Centrifuge GEA Wesffalia CTC 1 (WhisperFuge™)) with the reaction product from the container, at room temperature using a peristaltic pump (flow rate 3 l/min). After this first centrifugation, the solid obtained was collected in a container and neutralized with distilled water. To this end, volumes of distilled water were added consecutively, with constant stirring and controlling the pH of the mixture. The final volume of the mixture was about 50% the reaction volume and the pH value between 9 and 10. The obtained volume of neutralized mixture was centrifuged again, and the process of neutralization-centrifugation was repeated as described above until reaching a pH 7. Five cycles of centrifugation/neutralization were sufficient to achieve pH 7. The final product at pH 7 was washed with distilled water with stirring until complete disintegration of the solid. The final volume of this solution was approximately 25% of reaction volume. The mixture volume obtained was centrifuged again at room temperature and with a flow rate 3 l/min as described above. The product obtained in the above step was concentrated by discontinuous centrifugation, using an Eppendorf centrifuge 5804R. Finally, the product obtained was spray-dried with the following operating conditions and spray-drier specifications: Size of the atomization chamber=ø1200×745 mm; material in contact with the product=stainless steel AIS 316; outer material: AISI 304; cyclone=ø300; rotary rpms=24400 rpm; rotary power=3.5 kW rotary; maximum air rate (intake air)=990 m$^3$/h; maximum temperature of inlet air=250° C.; maximum power of air input batteries=27 kw; peristaltic pump for liquid inlet: automatic/manual speed.

The product resulting from the process described in this section is also named "DAMM product" or "Batch 1" in the following experiments.

The process was scaled at pilot scale, varying NaOH concentration from 1 M to 0.25 M. In vitro fat binding tests were performed to assess the maintenance of the biofunctionalities of the product in scaling, with positive results.

Example 2

Product Characterization

Figure 2A:
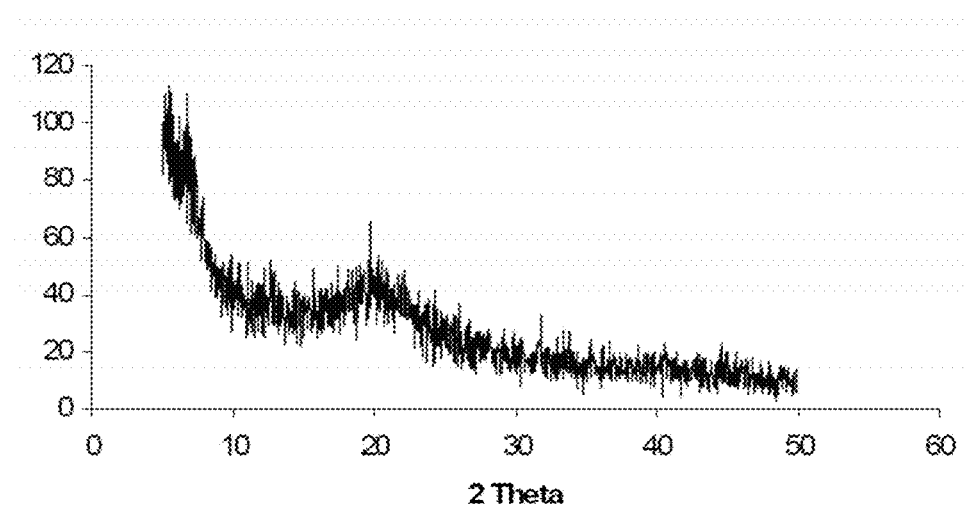
FIG. 2 shows the diffractograms (X-ray) of DAMM product (FIG. 2A) and pure chitin (chitin from crab shells Sigma, C3641) (FIG. 2B).
Figure 2B:
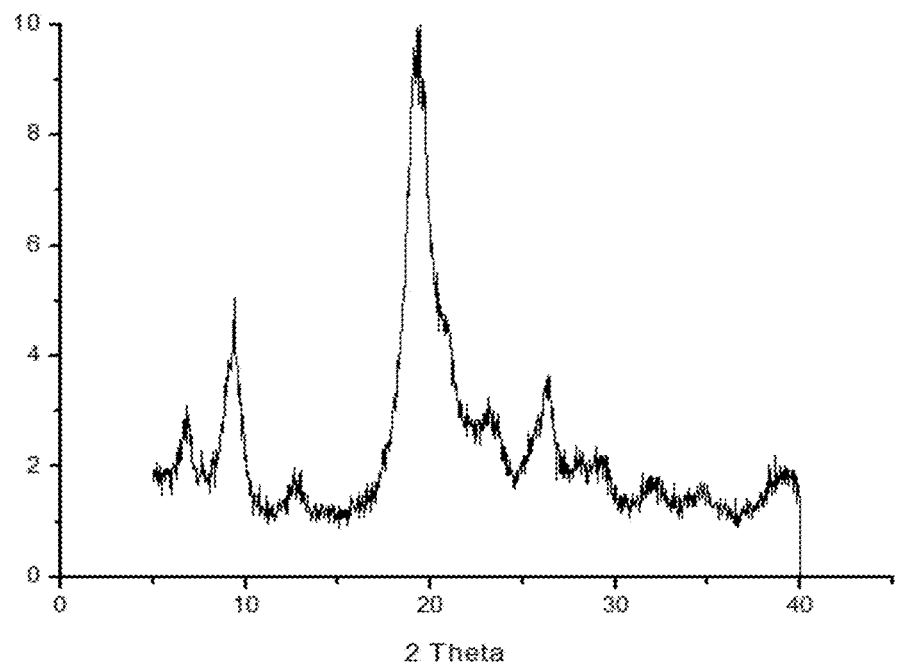
Figure 3:
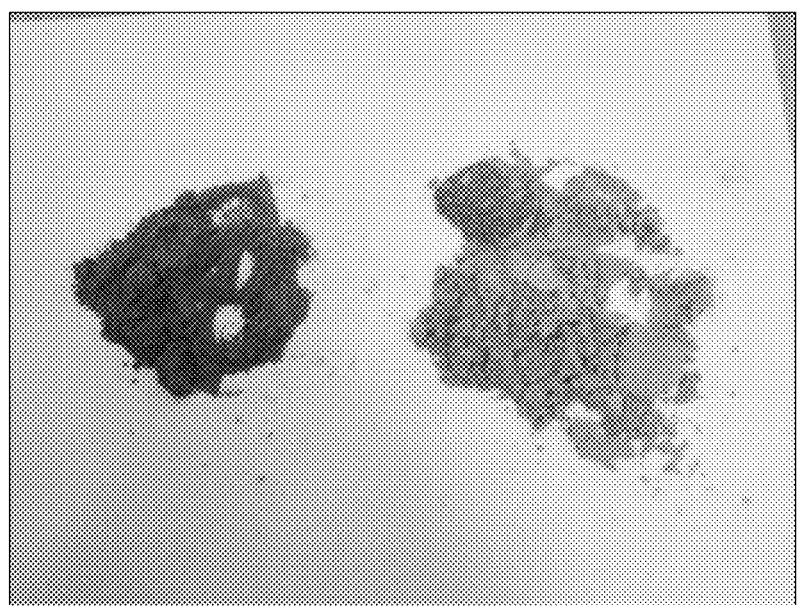
FIG. 3 shows the final product in form of light brown fine powder.

In FIG. 1 an $^1$H-NMR analysis showed that DAMM product obtained at pilot scale (lower figure) presents the same functional groups compared to the product obtained previously at laboratory scale (upper figure) (this product is called "060" in the figure). FIG. 2 shows the diffractograms (X-ray) of DAMM product (FIG. 2A) and pure chitin (FIG. 2B). FIG. 3 shows the appearance of DAMM product.

Chemical analysis showed that DAMM product had a ratio of chitosan, chitin and beta-glucan of 1:14:116 and an atomic mass percentage of carbon, hydrogen and nitrogen of 40.32%, 6.35% and 0.24% respectively. The solubility of the product at pH 3.5 in distilled water was 710 mg/l.

Example 3

Fat Binding Effects: In Vitro Selectivity Assays

Assays of fat binding and selectivity in the trapping of fats by GLC-MS were performed with the following lipids:
Olive oil+cholesterol (25 mg cholesterol/ml of olive oil)
Cotton seed oil
Fish oil+elaidic acid (2.5 mg elaidic acid/ml fish oil)
The arguments for using these fats and not others were:
They are complex mixtures of lipids, so information on the greater or lesser affinity for different types of fatty acids is obtained. Furthermore, the situation is close to a real intake.
The use of fish oil is very interesting to test the degree of affinity for docosahexaenoic acid (DHA) and eicosapentaenoic acid (EPA), which due to their significant health benefits it is interesting to avoid their immobilization.
The introduction of cholesterol in the assays with olive oil provides information on the ability to bind one of the most harmful fats from animal source.
With these products, the degree of capture affinity for a total of 16 fatty acids, more or less beneficial or harmful for cardiovascular health is assessed.
The "fatbinder" products tested were DAMM product, a commercial chitosan with 82% deacetylation degree from Primex ("Chitoclear", Iceland) ("Qs Primex") and glucan from *Laminaria* (*Laminaria digitata* Sigma, L9634).

The protocol used was as follows: For each fatbinder product to be tested, 12 ml of solution (w/v) at pH 2 with HCl 0.5 M were prepared. 3 g of lipids were added to this solution and stirred at 300 rpm for 3 hours at 37° C. The pH of the solution was then increased with 0.1 M NaOH to a first pH 6.2 and then to a maximum pH of 6.5 and maintained with agitation at 37° C. for 2.5 h. The solution was then centrifuged at 2000 g at 37° C. to separate the fat not bound to the product. The non-bound fat was removed with a pipette taking care of not aspirating aqueous phase. The solution was acidified with 0.5 M HCl to solubilize the fatbinder product and release as much fat as possible. The aqueous phase was extracted three times with 5 ml hexane and the three organic extracts were joined at the end to evaporate at 40° C. in a weighed container. The dried fat was finally weighed to quantify the amount of fat that the fatbinders were able to bind. The results are shown in TABLE 1.

TABLE 1

|  | % bound fat | mg bound fat/100 mg |
|---|---|---|
| Olive oil + cholesterol | | |
| Qs Primex | 29.4 ± 6.1 | 2015.8 ± 398.8 |
| Glucan (*Laminaria*) | 17.0 ± 5.7 | 1129.5 ± 374.8 |
| DAMM product | 24.1 ± 4.9 | 1615.6 ± 328.0 |
| Cotton seed oil | | |
| Qs Primex | 11.3 ± 1.2 | 746.8 ± 82.7 |
| Glucan (*Laminaria*) | 13.8 ± 5.3 | 944.2 ± 359.5 |
| DAMM product | 17.3 ± 7.3 | 1161.2 ± 490.9 |

TABLE 1-continued

|  | % bound fat | mg bound fat/100 mg |
|---|---|---|
| Fish oil + elaidic acid | | |
| Qs Primex | 78.7 ± 8.4 | 5364.4 ± 613.5 |
| Glucan (*Laminaria*) | 12.9 ± 3.9 | 894.1 ± 268.5 |
| DAMM product | 14.9 ± 6.0 | 998.2 ± 409.0 |

DAMM product shows a markedly lower fat binding capacity compared to Qs Primex in case of Fish oil+elaidic acid. This result is very relevant since it is interesting to avoid the immobilization of the components of Fish oil (DHA and EPA) because they are beneficial for health.

In the experiments of selective fat binding, a final value of % improvement was given. This value is obtained from subtracting the % of each fatty acid with the % presented by the untreated control. The results are shown in TABLES 2, 3 and 4. The sign is positive or negative depending on the health or toxicity of each fat. In the following tables, "tr" means traces; unsat=unsaturated; sat=saturated; monounsat=monounsaturated; polyunsat=polyunsaturated.

TABLE 2

| Olive oil + cholesterol | Myristic acid (sat) | Palmitic acid (sat) | Palmitoleic acid (monounsat) | Stearic acid (sat) | Oleic acid (monounsat) | Elaidic acid (unsat trans) | Linoleic acid (Polyunsat essential) | Linolenic acid (polyunsat) | Eicosanoic acid (sat) | Cholesterol | % improvement |
|---|---|---|---|---|---|---|---|---|---|---|---|
| Control without treatment | tr | 14 | 1.4 | 4.5 | 74.3 | — | 2.6 | 0.2 | — | 3.5 | |
| Qs Primex | tr | 12.3 | 0.9 | 4.4 | 77.4 | — | 1.7 | 0.3 | — | 2.8 | 2.1 |
| DAMM product | tr | 9.5 | 1.2 | 2.2 | 81.9 | — | 2.4 | — | — | 3.1 | 14.2 |

TABLE 3

| Cotton seed oil | Myristic acid | Palmitoleic acid | Palmitic acid | Fam Linolenic | Linoleic acid (polyunsat) | Oleic acid | Stearic acid | % improvement |
|---|---|---|---|---|---|---|---|---|
| Control without treatment | 0.7 | 0.5 | 22 | 0.2 | 49.8 | 23.5 | 3.3 | |
| Qs Primex | 0.3 | 2.4 | 25.5 | 0.6 | 47.9 | 21.0 | 2.2 | −4.1 |
| DAMM product | 0.7 | 0.6 | 20.5 | tr | 55.0 | 21.7 | 3.4 | 4.3 |

TABLE 4

| Fish oil + elaidic acid | Myristic acid | Palmitoleic acid | Palmitic acid | Linoleic acid | Elaidic acid | Oleic acid | Stearic acid | Linolenic acid (polyunsat) | Octadecatetraenoic acid (polyunsat) |
|---|---|---|---|---|---|---|---|---|---|
| Control without treatment | 8.2 | 13.7 | 17.1 | 0.2 | 4.2 | 9.7 | 4.9 | 1.0 | 4.1 |
| Qs Primex | 11 | 16.5 | 21.7 | 0.2 | 3.6 | 10.1 | 5.1 | 0.5 | 4.1 |
| DAMM product | 9.4 | 14.9 | 19.2 | 0.1 | 2.6 | 9.2 | 2.3 | 0.8 | 4.1 |

| Fish oil + elaidic acid | Eicosapentonic acid (polyunsat) | Arachidonic acid (polyunsat) | Docosahexaenoic acid (polyunsat) | Fam DHA (polyunsat) | % improvement |
|---|---|---|---|---|---|
| Control without treatment | 14.1 | 1.9 | 18.4 | 2.4 | |
| Qs Primex | 13.7 | 0.9 | 7.8 | 4.9 | −3.2 |
| DAMM product | 15.9 | 1.9 | 17.1 | 2.4 | 1.8 |

The product which involves more substantial improvements regarding the lipid profile of intakes (and therefore of the diet) is the DAMM product.

Example 4

Fat Binding Effects: In Vivo Animal Assay 4.1 In Vivo Animal Assay

An animal study was performed to assess the ability of selective fat binding. The animal model chosen were female Dunkin Hartley guinea pigs because this model has a lipid metabolism profile, especially in case of HDL, LDL and VLDL cholesterol, very similar to human profile. Guinea pigs were 5-6 weeks years old and weighed 300-400 g. Animals were divided into different groups, each one of n=8:

- A negative control group with cellulose (product without fat binding capacity);
- A positive group with oat bran Santiveri® ("Crusca di Avena", soluble fiber; with supposed ability to reduce fat absorption);
- A group with Chitosan S product (low molecular weight, 50-1.000 kDa, minor viscosity, DG 70% minimum, Primex, Iceland);
- A group with Chitosan L product (high molecular weight, 500-5.000 kDa, DG 70% minimum, Primex, Iceland).

The assay took 35 days comprising 7 days of acclimation and 28 days of experimentation. Animals were in open individual cages, submitted to 12 h light/dark cycles, with water and feed ad libitum. To maximize the observation of differences, a customized hypercaloric diet added to the feed and rich in fats and simple sugars: 4.7 kcal vs 3.8 kcal. For the addition of 12% of each of the products to be tested (cellulose/Santiveri®/DAMM product/Chitosan S/Chitosan L), a basal feed was used to maximize the possible effects of each of the experimental products. The results are shown in TABLE 5.

The results summarized in the Table 5 show that animals fed with DAMM product showed a less weight increase compared to the control groups Santiveri® and cellulose. The energy efficiency (g gained per kcal of ingested feed) is the value which clearly shows product efficacy in reducing absorption. The value in kcal eliminates possible differences between feeds due to their composition. Thus, DAMM product reduced total fat absorption measured as total feed efficiency (g of body weight gained per kcal ingested), compared to cellulose and the positive control.

Chitosan S shows a major reduction than DAMM product, but DAMM product presents the slightest deviation in values. It can be observed that Santiveri® and the negative control have a similar performance.

4.2. Analysis of Feces

The study was followed by the analysis of feces, as ratification of the ability of the products to reduce fat absorption and to elucidate the ability to bind preferentially one or another fat. The values to be analyzed were:

- Production of feces: interesting to infer the operating mechanism and potential nuisance to consumers
- Apparent absorption: calculated as grams of dry matter absorbed per 100 g of dry feed consumed
- Total excretion: calculated as grams of dry matter excreted per 100 grams of dry matter consumed
- Analysis of fatty acids in feces: calculated as concentration of fatty acids and amount excreted throughout the different weeks of the experiment The comparison of the results took place through a cross-sectional analysis groups. The statistical test used was the Duncan multiple comparison (p≤0.05). The results are expressed as grams of fresh feces excreted per guinea pig and per day (n=8) in the case of excretion, and as grams of feces in dry weight per guinea pig and day (n=8) in the case of dry matter. The results are shown in TABLE 6.

TABLE 5

|  | Cellulose | | | Santiveri® | | | Chitosan S | | | Chitosan L | | | DAMM prod. | | |
| --- | --- | --- | --- | --- | --- | --- | --- | --- | --- | --- | --- | --- | --- | --- | --- |
|  | Mean | SD | | Mean | SD | | Mean | SD | | Mean | SD | | Mean | SD | |
| Initial weight (g) | 401.4 | 19.8 | | 407.3 | 23.3 | | 406.8 | 15.0 | | 400.3 | 16.0 | | 397.2 | 18.4 | |
| Final weight (g) | 557.7 | 29.9 | BC | 570.8 | 47.0 | C | 510.2 | 55.7 | B | 430.9 | 42.8 | A | 515.0 | 40.7 | B |
| Weight increase (g) | 156.3 | 24.9 | C | 163.5 | 29.6 | C | 103.4 | 45.1 | B | <u>30.6</u> | 39.8 | A | 117.9 | 32.3 | B |
| Efficiency (g/100 g) | 21.5 | 2.6 | CD | 23.1 | 3.3 | D | 14.4 | 5.3 | B | 4.6 | 5.4 | A | 17.1 | 4.2 | BC |
| Efficiency (g/100 kcal) | 5.2 | 0.6 | C | 5.3 | 0.7 | C | 3.5 | 1.3 | B | <u>1.1</u> | 1.3 | A | 4.2 | 1 | BC |

Feed efficiency (g/100 g) is the animal weight increase in grams per 100 g of ingested feed. Feed efficiency in g/100 kcal is the increase of animal body weight in grams per 100 kcal ingested. The comparison of the results took place through a cross-sectional analysis groups. The statistical test used was the Duncan multiple comparison (p≤0.05). Samples showing different letters show statistically significant differences.

As it can be seen in the Table 5, the effects of Chitosan L product on weight gain and efficiency (underlined results) are abnormally high, bordering toxicity. Chitosan L caused relevant intestinal problems to animals and diarrhea. Thus, it can be said that Chitosan L produces anti-nutritional non desirable effects. This fact implies that the inclusion of this group in the analysis mask the results. Consequently it was decided to exclude the Chitosan L group from the statistical analysis.

TABLE 6

Samples showing different letters show statistically significant differences.

| Week | Product | Excretion | | | % Humidity | | | Dry matter | | |
| --- | --- | --- | --- | --- | --- | --- | --- | --- | --- | --- |
| | | Mean | SD | | Mean | SD | | Mean | SD | |
| 0 | Cellulose | 26.8 | 6.2 | | 60.2 | 8.1 | | 10.3 | 1.5 | |
| | Santiveri® | 26.1 | 9.2 | | 59.5 | 10.2 | | 9.9 | 2.2 | |
| | Chitosan S | 28.2 | 9.9 | | 58.5 | 11.2 | | 10.9 | 2.0 | |
| | DAMM prod. | 26.0 | 8.3 | | 57.3 | 16.6 | | 10.3 | 2.4 | |
| 1 | Cellulose | 7.2 | 2.7 | AB | 56.4 | 6.4 | | 3.0 | 0.9 | AB |
| | Santiveri® | 6.1 | 1.8 | A | 59.9 | 15.6 | | 2.3 | 0.7 | A |
| | Chitosan S | 14.2 | 4.4 | B | 59.0 | 5.8 | | 5.9 | 2.1 | C |

TABLE 6-continued

Samples showing different letters show statistically significant differences.

| Week | Product | Excretion | | | % Humidity | | | Dry matter | | |
|---|---|---|---|---|---|---|---|---|---|---|
| | | Mean | SD | | Mean | SD | | Mean | SD | |
| | DAMM prod. | 8.2 | 2.0 | AB | 58.1 | 12.8 | | 3.3 | 0.6 | AB |
| 4 | Cellulose | 7.6 | 3.1 | A | 70.4 | 3.8 | A | 2.2 | 0.9 | A |
| | Santiveri ® | 5.8 | 2.2 | A | 73.1 | 4.8 | A | 1.5 | 0.4 | A |
| | Chitosan S | 17.5 | 3.9 | B | 53.3 | 5.3 | C | 8.1 | 1.6 | B |
| | DAMM prod. | 10.4 | 2.3 | A | 74.0 | 6.1 | A | 2.7 | 0.7 | A |

Consumption of DAMM product did not imply a significant increase in fecal excretion in animals. Extrapolating this to the potential human consumption, it means that there would be no inconvenience in this regard. It is also important to note that the stool had a good look. The same cannot be said in the Chitosan S group (See Table 6).

At week, there were no statistically significant differences in any case. At week 1, in "Excretion", DAMM product did not differ from any other group. DAMM product did showed differences in the value of dry matter vs the Chitosan S group. At week 4, DAMM group, the cellulose group and the Santiveri® group significantly differed from the Chitosan S group. Thus, the consumption of feed with DAMM product, although slightly increased excretion, it was not statistically significant, unlike the Chitosan S product. This is an interesting point, because increasing the excretion of feces is not negative, but always if takes place within normal parameters, which is not the case of the Chitosan S product.

Chitosan S product reaches extraordinarily high values of excretion and dry matter. This fact, unlike what happens with DAMM product implies that there is a non-selective effect but an action by physical methods: Chitosan S product would not specifically bind fat, but many more nutrients. Consequently, the excretion is increased and weight gain is lower. In view of the high values in dry matter obtained by the Chitosan S group, it seems clear that its biofunctionality is due to the increase in the viscosity of the alimentary bolus. This is a physical method which involves an increased removal of fat and a reduced possibility of absorption. Consequently, Chitosan S is a product without specific fat binding capacity which could lead to antinutritional effects.

Since values in dry matter of the negative control (cellulose), the commercial (Santiveri®) group and DAMM group are very similar (not significantly different) and on the other hand, weight gain values, as shown, are different, it can be inferred that fat excretion is really higher in DAMM group. Chitosan S group values reaffirm the non-specificity in excretion consequence of physical methods.

4.3. Lipid Composition of Feces

Finally, lipid composition of the feces of animals was analyzed to assess whether they were differences regarding the degree of excretion of certain lipids. Statistical analysis was performed according to the multiple comparison test of Duncan (p 0.05).

At week 0 there was no difference between groups, so the baseline was the same for all states and each of the groups. The fatty acid analysis at week 4 is shown in TABLE 7, where results are expressed as mg of fatty acids per g of feces and in TABLE 8, where results are expressed as mg of excreted fatty acids per animal and per day.

TABLE 7 results expressed as mg of fatty acids per g of feces

| | Cellulose | | | Santiveri ® | | | Chitosan S | | | DAMM product | | |
|---|---|---|---|---|---|---|---|---|---|---|---|---|
| | Mean | SD | | Mean | SD | | Mean | SD | | Mean | SD | |
| C12:0 | 7.91 | 2.35 | A | 10.18 | 2.22 | A | 30.04 | 5.58 | B | 10.72 | 2.29 | A |
| C14:0 | 9.95 | 1.57 | A | 14.23 | 3.03 | B | 19.34 | 2.00 | C | 14.90 | 2.42 | B |
| C16:0 | 57.71 | 8.42 | A | 86.38 | 23.87 | A | 48.48 | 2.59 | A | 85.46 | 17.84 | B |
| C18:0 | 108.40 | 20.65 | B | 137.76 | 13.79 | C | 44.88 | 3.19 | A | 152.30 | 23.32 | C |
| C20:0 | 2.82 | 0.33 | B | 3.23 | 0.16 | C | 1.54 | 0.12 | A | 3.13 | 0.33 | C |
| C22:0 | 1.70 | 0.20 | B | 1.89 | 0.09 | B | 1.05 | 0.29 | A | 1.64 | 0.63 | B |
| C24:0 | 1.16 | 0.19 | B | 1.34 | 0.09 | C | 0.59 | 0.05 | A | 1.37 | 0.20 | C |
| TSFA | 189.66 | 25.49 | B | 255.02 | 32.73 | C | 145.92 | 9.69 | A | 269.53 | 36.47 | C |
| C16:1n7 | 0.16 | 0.06 | A | 0.21 | 0.04 | AB | 1.11 | 0.21 | C | 0.35 | 0.05 | B |
| C18:1n9 | 10.18 | 3.10 | A | 13.59 | 2.14 | A | 53.35 | 8.27 | B | 12.68 | 2.23 | A |
| C18:1n7 | 1.11 | 0.45 | A | 1.32 | 0.22 | A | 3.51 | 0.43 | B | 1.45 | 0.37 | A |
| C20:1n9 | 0.39 | 0.10 | A | 0.55 | 0.09 | C | 0.68 | 0.06 | D | 0.48 | 0.05 | B |
| MUFA | 11.68 | 3.62 | A | 15.46 | 2.41 | A | 57.64 | 8.75 | B | 14.61 | 2.62 | A |
| C18:2n6 | 10.65 | 3.97 | A | 12.08 | 2.14 | A | 71.83 | 13.30 | B | 10.64 | 3.33 | A |
| C18:3n3 | 0.26 | 0.05 | A | 0.29 | 0.04 | A | 0.92 | 0.14 | B | 0.27 | 0.04 | A |
| PUFA | 10.91 | 4.02 | A | 12.37 | 2.18 | A | 72.75 | 13.44 | B | 10.90 | 3.37 | A |
| TUFA | 22.59 | 7.63 | A | 27.83 | 4.57 | A | 130.39 | 21.84 | B | 25.51 | 5.82 | A |
| TOTAL | 212.25 | 28.24 | A | 282.85 | 34.61 | B | 276.31 | 30.02 | B | 295.04 | 35.34 | BC |
| TUFA/TSFA | 0.12 | 0.04 | A | 0.11 | 0.02 | A | 0.89 | 0.11 | B | 0.10 | 0.03 | A |
| n6/n3 | 40.45 | 7.97 | A | 41.58 | 3.15 | A | 77.95 | 3.11 | B | 39.37 | 8.18 | A |

C18:1 trans (sum of isomers trans)
TSFA: total of saturated fatty acids
MUFA: total of monounsaturated fatty acids (no trans)
PUFA: total of polyunsaturated fatty acids (no trans)
TUFA: total of unsaturated fatty acids In comparison with the negative control (cellulose) DAMM product showed higher values of fatty acids which have a negative potential effect for health (saturated). In contrast, the most of monounsaturated and polyunsaturated fatty acids did not showed significant differences.

TABLE 8 results expressed as mg of excreted fatty acids per animal and per day.

| | Cellulose | | | Santiveri ® | | | Chitosan S | | | DAMM product | | |
|---|---|---|---|---|---|---|---|---|---|---|---|---|
| | Mean | SD | | Mean | SD | | Mean | SD | | Mean | SD | |
| C12:0 | 17.80 | 8.46 | A | 15.40 | 5.61 | A | 245.82 | 67.91 | B | 27.94 | 7.17 | A |
| C14:0 | 22.20 | 9.24 | A | 21.40 | 7.33 | A | 157.52 | 38.08 | B | 39.31 | 10.56 | A |
| C16:0 | 128.40 | 56.72 | A | 127.78 | 42.73 | A | 391.61 | 79.13 | C | 225.05 | 58.67 | B |
| C18:0 | 231.92 | 80.81 | A | 208.71 | 75.87 | A | 359.89 | 62.10 | B | 411.63 | 145.92 | B |
| C20:0 | 6.13 | 2.13 | AB | 4.80 | 1.31 | A | 12.38 | 2.45 | C | 8.25 | 1.79 | B |
| C22:0 | 3.68 | 1.28 | A | 2.80 | 0.68 | A | 8.49 | 2.98 | B | 4.20 | 1.71 | A |
| C24:0 | 2.50 | 0.83 | A | 1.98 | 0.46 | A | 4.74 | 0.83 | C | 3.62 | 0.87 | B |
| TSFA | 390.43 | 143.02 | A | 361.47 | 115.72 | A | 1022.93 | 209.17 | C | 680.69 | 199.30 | B |
| C16:1n7 | 0.37 | 0.19 | A | 0.31 | 0.11 | A | 9.07 | 2.56 | B | 0.92 | 0.14 | A |
| C18:1n9 | 22.82 | 10.90 | A | 20.40 | 6.76 | A | 435.13 | 113.54 | B | 33.12 | 7.58 | A |
| C18:1n7 | 2.43 | 1.19 | A | 2.02 | 0.76 | A | 28.52 | 6.75 | B | 3.76 | 0.91 | A |
| C20:1n9 | 0.84 | 0.31 | A | 0.82 | 0.25 | A | 5.54 | 1.21 | B | 1.28 | 0.37 | A |
| MUFA | 26.08 | 12.35 | A | 23.24 | 7.75 | A | 469.94 | 121.64 | B | 38.16 | 8.79 | A |
| C18:2n6 | 23.74 | 12.24 | A | 18.19 | 6.31 | A | 589.90 | 168.87 | B | 27.90 | 10.62 | A |
| C18:3n3 | 0.56 | 0.21 | A | 0.43 | 0.13 | A | 7.52 | 2.05 | B | 0.70 | 0.18 | A |
| PUFA | 24.31 | 12.44 | A | 18.62 | 6.44 | A | 597.41 | 170.91 | B | 28.60 | 10.76 | A |
| TUFA | 50.39 | 24.74 | A | 41.86 | 14.18 | A | 1067.36 | 291.36 | B | 66.76 | 19.17 | A |
| TOTAL | 440.82 | 161.82 | A | 403.33 | 128.21 | A | 2090.28 | 496.10 | B | 747.45 | 209.40 | A |
| TUFA/TSFA | 0.12 | 0.04 | A | 0.11 | 0.02 | A | 0.89 | 0.11 | B | 0.10 | 0.03 | A |
| n6/n3 | 40.45 | 7.97 | A | 41.58 | 3.15 | A | 77.95 | 3.11 | B | 39.37 | 8.18 | A |

The excretion of saturated fatty acids was significantly increased after DAMM product consumption. That of monounsaturated fatty acids was increased, although results were not statistically significant, whereas that of polyunsaturated fatty acids did not increase.

In view of the results, DAMM product implies a higher excretion of saturated fatty acid: C14:0/C16:0/C18:0/C20:0/C22:0 (myristic acid, palmitic, stearic, arachidic, behenic acids). This is positive because a reduction in the absorption of saturated fatty acids implies an improvement in the nutritional profile of the diet. As a consequence of this reduction, it is found a statistically significant reduction of absorption of total saturated fatty acids (TSFA).

Regarding linoleic acid (C18:2n6) and α-linolenic acid (C18:3n3), no statistically significant increase was observed in DAMM group. This represents another interesting biofunctionality for a selective fat binding product, since linoleic and linolenic acids are essential fatty acids and important for health. To strengthen the observed values, the results confirm that there is no an increased excretion in the total polyunsaturated and unsaturated fatty acids. Conversely, there is a net reduction in the total absorption of fatty acids, so DAMM product is a product that reduces fat absorption but does not increase the excretion of the fatty acids which are beneficial for health.

Santiveri® product has a good performance (similar to DAMM product) as regards selectivity, as seen in the statistical results of the values expressed as mg of fatty acids per gram of feces. However, in the daily excretion levels, its behavior is not the desirable: their excretion values are low, which explains the lack of effect observed in the Feed Efficiency and Weight gain values. Chitosan S product shows the opposite of that reported for the product Santiveri® as concerned to fatty acid analysis: fat binding capacity is not selective and it causes large amounts of excreted fat, by its high feces production.

Example 5

Fat Binding Effects: Functional Clinical Assay in Humans

The study was a clinical, randomized, double-blind, placebo-controlled study with parallel groups, to study the efficacy and safety of DAMM product as dietary supplement in weight control. The sample size was 60 patients divided into two parallel study groups of 30 participants, one received active substance (DAMM product) dissolved in water, while the other received placebo dissolved in water. Patients enrolled were adults with a body mass index moving between overweight and obesity (25-34.99 Kg/m$^2$), without eating disorders and without following or have followed a low calorie diet in the three preceding months. The recruitment was not easy due to the mentioned requirements, patients had to be people who came as the first consultation and if not, who surely would not have been prescribed a diet or some type of dietary intervention. Difficulties in recruiting led to a multi-center trial. The clinical protocol was approved by the Ethics Committee of Hospital Clinic de Barcelona, Centro Clínico Diagnóstico of Madrid and Instituto Médico Europeo de la Obesidad of Madrid.

The objective was to demonstrate that consumption of DAMM product improved weight people (BMI ultimately). In order to provide adequate follow up of the evolution of patients, the study was over 12 weeks (84 days) with an intermediate assessment at 42 days. The study recruited 60 participants (11 men and 49 women with a mean age of 48 years (22 to 65 years)). 44 of them completed the study. Of the patients who abandoned the study, most of them were due to personal reasons. General dietary recommendations for a healthy Mediterranean-type diet (eucaloric) were given to the participants, who followed them for 1 month before the start of the experimental phase, noting deviations from the diet in which incurred. An ANOVA analysis resulted in no statistically significant differences in the demographic characteristics or in the clinical basal characteristics of participants. Thus, results obtained at the end of the trial are the result of the effect of product without influences of patients distribution.

DAMM product was presented in screw caps adaptable to liquid bottles. The products under study were (composition per screw cap):

Experimental product: 1 g of DAMM product+35 mg "caramelina" colorant (E-102/124/132 16%)

Control: Placebo: 1 g of microcrystalline cellulose+17.5 mg colorant (E-102/124/132 16%)

Each subject dissolved 2 caps in a bottle of 500 ml of water and took it with lunch and dissolved 1 cap in a bottle of 500 ml and took it with dinner. The procedure was repeated daily for 12 weeks. Each participant performed 3 visits to the study center during the experimental phase, one at time 0 (visit 0 or baseline), an intermediate visit and one at the end of study. In each visit, different parameters were analyzed as weight and height measures, anthropometric measurements (waist and hip circumference), percentage of body fat (measured by dual-energy X-ray absorptiometry), and blood tests.

TABLE 9

Results on weight (kg). SD = Standard deviation; MSE = Median standard error

Experimental group

|  | Mean | N | SD | MSE |
|---|---|---|---|---|
| Baseline | 78.6737 | 19 | 15.15724 | 3.47731 |
| Final | 78.0105 | 19 | 14.83925 | 3.40436 |

|  | Mean | SD | MSE | P |
|---|---|---|---|---|
| Baseline – final | 0.66316 | 1.20149 | 0.27564 | 0.027 |

Placebo

|  | Mean | N | SD | MSE |
|---|---|---|---|---|
| Baseline | 76.1909 | 22 | 8.61847 | 1.83746 |
| Final | 77.5955 | 22 | 8.84746 | 1.88629 |

|  | Mean | SD | MSE | P |
|---|---|---|---|---|
| Baseline – final | −1.40455 | 1.51986 | 0.32404 | 0.000 |

Intra-group comparison: After taking DAMM product for 3 months, a weight reduction of 0.7 kg was shown. The difference between baseline and final values was statistically significant with $p=0.027$. In the placebo group statistically significant differences existed but for weight gain, with $p=0.000$.

Inter-group comparison: By comparing differences in weight of the participants receiving DAMM product vs. receiving placebo, it was found that these differences were statistically significant with $p=0.000$.

TABLE 10

Results on waist circumference (cm). SD = Standard deviation; MSE = Median standard error Experimental group

|  | Mean | N | SD | MSE |
|---|---|---|---|---|
| Baseline | 96.8684 | 19 | 10.07037 | 2.31030 |
| Final | 94.8000 | 19 | 11.30555 | 2.59367 |

|  | Mean | SD | MSE | P |
|---|---|---|---|---|
| Baseline – final | 2.06842 | 3.27703 | 0.75180 | 0.013 |

Placebo

|  | Mean | N | SD | MSE |
|---|---|---|---|---|
| Baseline | 99.7000 | 20 | 7.77208 | 1.73789 |
| Final | 99.9750 | 20 | 7.77221 | 1.73792 |

|  | Mean | SD | MSE | P |
|---|---|---|---|---|
| Baseline – final | −0.27500 | 2.39228 | 0.53493 | 0.613 |

Intra-group comparison: There was a decrease in waist circumference after taking DAMM product. The difference of 2 cm reduction in waist circumference between baseline and final values were statistically significant with $p=0.013$. No statistically significant differences were observed for the placebo group.

Inter-group comparison: By comparing differences in waist circumference of the participants receiving DAMM product vs. receiving placebo, it was found that these differences were statistically significant with $p=0.015$.

TABLE 11

Results on body fat (%) SD = Standard deviation; MSE = Median standard error

Experimental group

|  | Mean | N | SD | MSE |
|---|---|---|---|---|
| Baseline | 42.5105 | 19 | 7.46636 | 1.71290 |
| Final | 41.6947 | 19 | 7.91345 | 1.81547 |

|  | Mean | SD | MSE | P |
|---|---|---|---|---|
| Baseline – final | 0.81579 | 1.82521 | 0.41873 | 0.067 |

Placebo

|  | Mean | N | SD | MSE |
|---|---|---|---|---|
| Baseline | 40.9773 | 22 | 7.15960 | 1.52643 |
| Final | 40.9727 | 22 | 7.06050 | 1.50530 |

|  | Mean | SD | MSE | P |
|---|---|---|---|---|
| Baseline – final | 0.0045 | 1.31529 | 0.28042 | 0.987 |

A reduction of 0.82% of total body fat was observed after taking DAMM product. This decrease had a trend to statistical significance with $p=0.067$. No statistically significant differences in body fat were observed for the placebo group.

It was observed a reduction of 1% of android (upper body) fat in the group of DAMM product, but this difference was not statistically significant, $p=0.101$. The product also decreased body fat percentage, i.e. a 0.8% of loss of body fat and a reduction of almost 1% of fat android. These results were not statistically significant because the sample size was not large enough to detect differences between groups, but is clinically important. The reduction of the body fat and android fat percentage corresponds to a redistribution of body fat, reducing its accumulation in the abdominal area. This is related to a potential benefit in reducing cardiovascular risk factors, hypertension and diabetes. Probably significant differences could have been found with a larger N. No statistical significant variations were observed in hip perimeter and in gynoid fat (lower body) after taking DAMM product and in the placebo group. With these results it can be inferred that DAMM product promotes weight loss, with a reduction of approximately 2.1 kg weight and a waist circumference reduction of 2 cm at 3 months of treatment. These results are clinically relevant since the results of decreased weight and waist circumference were obtained in the absence of specific restrictive diet and in a short time of treatment (3 months). The survey about the product given to the participants revealed that they were satisfied with the taste and pleasant smell of the product.

Example 6

Glucose Binding Effect: Oral Glucose Tolerance Test in Animal Model

Experiments of "oral glucose tolerance test" (OGTT) allow to analyze the effect of certain compounds in response to glucose ingestion. In spite of the name ("oral") the experiments can also be performed by intragastric administration, as in this case. The protocol was as follows: 24 male Sprague-Dawley rats weighing between 250-300 g were fasting overnight (14 to 16 h). Food was removed and animals were relocated in clean cages to prevent intake of stool. Water was provided ad libitum during all the experiment. The day of the experiment, after fasting, the animals were weighed. The compounds to be tested were mixed at predetermined doses with the dose of glucose chosen to finally intragastric administer 1 ml of treatment/200 g animal (i.e. 2 g glucose/kg animal). Guar gum was used as positive control due to be recognized as glucobinder. The test groups were the following:

Positive control: guar gum (6 mg/ml)+glucose (400 mg/ml) to 1 ml per 200 g of animal); n=8

Negative control: glucose (400 mg/ml to 1 ml per 200 g of animal); n=8

DAMM group: DAMM product (6 mg/ml)+glucose (400 mg/ml to 1 ml per 200 g of animal); n=8

Once the solutions were prepared, the value of basal glycemia of all animals (corresponding to time 0) was determined using a Glucometer® Elite. The different treatments were administered by intragastric administration to each group of animals. The timer was activated after administration to the first animal in each group. Glucose levels were determined at time 15, 30, 60 and 120 min. After the last measurement of glycemia, feeding to animals was restored, according to the instructions of the Ethics Committee.

TABLE 12

Results are expressed as media in mg/dl ± S.D.; AUC means incremental area under the curve; results in the same row with different letters denote significant differences based on the Duncan multivariate test with $p \leq 0.05$.

|  | Negative control | Positive control (guar gum) | DAMM product |
|---|---|---|---|
| Animal weight (g) | 370.8 ± 24.6 | 363.2 ± 19.8 | 366.1 ± 20.7 |
| Time (min) |  |  |  |
| 0 | 92.89 ± 9.21 | 89.2 ± 11.57 | 87.9 ± 7.67 |
| 15 | 132.11 ± 16.12 A | 115.2 ± 8.53 B | 120.3 ± 13.34 AB |
| 30 | 136.89 ± 29.67 | 122 ± 13.3 | 126.6 ± 15.69 |
| 60 | 137.22 ± 21.76 | 128 ± 10.9 | 132.2 ± 6.54 |
| 120 | 128.22 ± 15.52 | 119.5 ± 10.48 | 116 ± 21.15 |
| Increase 15 min | 39.22 ± 19.61 | 26 ± 16.76 | 32.4 ± 12.71 |
| Increase 30 min | 44 ± 30.83 | 32.8 ± 22.72 | 38.7 ± 16.28 |
| Increase 60 min | 44.33 ± 24.28 | 38.8 ± 15.08 | 44.3 ± 13.28 |
| Increase 120 min | 35.33 ± 15.58 | 30.3 ± 16.68 | 28.1 ± 24.32 |
| AUC 30 min | 918 ± 471 | 636 ± 415 | 776 ± 296 |
| AUC 60 min | 2243 ± 1245 | 1710 ± 931 | 2021 ± 632 |
| AUC 120 min | 4633 ± 2135 | 3783 ± 1804 | 4229 ± 1358 |

Differences between the values observed in the first points of the kinetic values showed statistically significance: this is the point more interesting in detecting differences between groups as it is the peak where the increase in sugar concentration vs. the previous point (baseline) is more pronounced. At this postprandial time is where glucose peaks show a greater increase and therefore represent a major health risk. Without achieving statistical significance, it can be clearly seen that at times 90 and 120 min there is an inversion in the relative positions of the curves of the positive control and DAMM product.

DAMM product does not show a greater effect in the glucose reduction with respect to the positive control with guar gum but the results are satisfactory because DAMM product is able to control glucose levels. DAMM product has a relevant advantage over guar gum since the latter increases very significantly the viscosity of the solutions, so it is the "mechanical trapping" which glucose suffers that explains this reduction in blood peak. On the contrary, DAMM product does not alter viscosity of a solution, representing a very relevant fact in food technology. The product is adequate for diabetics since glucose peak is lower and for sports since the peak is more sustained over time.

Example 7

Detoxifying Effect

The sequestering power of DAMM product against different toxics was analyzed. Different fractions obtained from a second thermoalcaline treatment starting with DAMM product were also tested for their detoxifying ability. The name of each fraction indicates the specific treatment conditions of said second thermoalcaline treatment. For all cases, the % of sequestered compound was determined using the following calculation: % of sequestered compound=100 (1−XFx/Xref)×100

XFx is the experimental compound concentration for each fraction x, and Xref is the theoretical compound concentration. The amount of sequestered compound per mg of DAMM product fraction was determined by the following formula:

$$(Xref-XFx) \times Vx/Mr = X \text{ ng sequestered compound/mg DAMM product fraction}$$

Vx is the volume of fraction and Mr the molecular weight of the compound tested.

7.1. Aflatoxin B1 Analysis

Aflatoxin B1 (AFB1) is a subtype of mycotoxin produced by members of the genus *Aspergillus* such as *Aspergillus flavus* and *Aspergillus parasiticus*. It can be a contaminant of several foods. The metabolism of AFB1 leads to one of the most potent carcinogen. For the analysis, each of DAMM product fractions was dispensed (in independent experiments) in a test tube at a concentration of 1 mg/ml in distilled water. 0.9 ml of standard solution of AFB1 (0.9 mg of AFB1) were added to a final volume of 17.9 ml. The theoretical final concentration of AFB1 in the test suspension was 50.3 μg/ml (50.3 ppm). Three identical tubes were prepared as controls without adding DAMM product fractions. The mixture was incubated at 37° C. with agitation at 300 rpm for 3 hours. Then the product was filtered through a syringe of 0.45 μm pore diameter. The sequestered AFB1 was finally determined by HPLC-FD.

7.2. Mercury (Hq) Analysis

Each of the fractions was dispensed (two replicates) in a test tube at a concentration of 1 mg/ml in distilled water (20 mg of each fraction with 19 ml of distilled water). Then, 1 ml mercuric chloride solution (0.560 mg of Hg) was added reaching a final volume of test solution of 20 ml. The theoretical final concentration of Hg in the test solution was 28.00 μg/ml (28.00 ppm). Three identical tubes were prepared as controls without adding DAMM product fractions. The mixture was incubated at 37° C. with agitation at 300 rpm for 3 hours. Then the product was filtered through a syringe of 0.45 μm pore diameter. The sequestered Hg was finally determined. Hg sequestration values were surprisingly good, as shown in TABLE 13.

7.3. Polychlorinated Biphenyls

The compound PCB 209 (decachlorobiphenyl) was use as a model of those polychlorinated biphenyls (PCB) found in the environment as it is one of the most abundant and toxic. Each of the fractions was dispensed (two replicates) in a test tube at a concentration of 1 mg/ml in dichloromethane (10 mg of each fraction with 10 ml of dichloromethane). 0.1 ml of PCB 209 stock solution (55 μg PCB 209) was added to the previous solution. The theoretical final concentration of PCB 209 in the test solution was 5.5 μg/ml. Three identical tubes were prepared as controls without adding DAMM product fractions. The mixture was incubated at 30° C. with agitation at 300 rpm for 3 hours. Then the product was filtered through a syringe of 0.45 μm pore diameter. The sequestered PCB 209 was finally determined.

7.4. Furan

Each of the fractions were dispensed (in independent experiments) in a test tube at a concentration of 1 mg/ml in dichloromethane (10 mg of each fraction with 10 ml of dichloromethane). 0.1 ml of furan stock solution (55 μg furan) was added to the previous solution. The theoretical final concentration of furan in the test solution was 5.5 μg/ml. Three identical tubes were prepared as controls without adding DAMM product fractions. The mixture was incubated at 30° C. with agitation at 300 rpm for 3 hours. Then the product was filtered through a syringe of 0.45 μm pore diameter. The sequestered furan was finally determined. Results for all the analyzed toxics are shown in TABLE 13.

TABLE 13

| Fraction | % capture AFB1 | % capture Hg | % capture PCB 209 | % capture Furan | Mean (%) |
|---|---|---|---|---|---|
| DAMM product | 12.4 | 55.4 | 16 | 25 | 19.3 |
| Fraction 2 (30 min 80° C. NaOH 50%) | 17.7 | 30.3 | 0 | 14 | 10.3 |
| Fraction 3 (120 min 80° C. NaOH 50%) | 20.9 | 50.3 | 17 | 5 | 16.3 |
| Fraction 4 (240 min 80° C. NaOH 50%) | 18.1 | 18.1 | | | |
| Fraction 5 (30 min 80° C. NaOH 25%) | 16 | 50.3 | 2 | 8 | 13.05 |
| Fraction 6 (120 min 80° C. NaOH 25%) | 8.5 | 18.5 | | | |
| Fraction 7 (240 min 80° C. NaOH 25%) | 22.9 | 29.1 | 9 | 10 | 12.5 |
| Fraction 8 (30 min 40° C. NaOH 50%) | 13.8 | 33.8 | | | |
| Fraction 9 (120 min 40° C. NaOH 50%) | 27.1 | 66.7 | 13 | 6 | 18.8 |
| Fraction 10 (240 min 40° C. NaOH 50%) | 9.5 | 35.4 | | | |
| Fraction 11 (30 min 40° C. NaOH 25%) | 15.3 | 32.2 | 22 | 11 | 15.42 |
| Fraction 12 (120 min 40° C. NaOH 25%) | 0 | 38.0 | 20 | 6 | 13.10 |
| Fraction 13 (240 min 40° C. NaOH 25%) | 0 | 28.3 | | | |
| Fraction 14 (30 min 60° C. NaOH 37.5%) | 0 | 42.4 | | | |
| Fraction 15 (135 min 60° C. NaOH 37.5%) | 6.7 | 31.1 | | | |
| Fraction 16 (240 min 60° C. NaOH 37.5%) | 0.3 | 24.8 | | | |
| Fraction 17 (135 min 80° C. NaOH 37.5%) | 0 | 22.8 | | | |
| Fraction 18 (135 min 40° C. NaOH 37.5%) | 0 | 38.9 | | | |
| Fraction 19 (135 min 60° C. NaOH 50%) | 2.1 | 26 | | | |
| Fraction 20 (135 min 60° C. NaOH 25%) | 3.5 | 25.2 | | | |

Not all the fractions were tested against all the toxics as it is seen in the Table 13. Despite this fact, they cannot be disregarded because they can be interesting for being active against a particular toxic. For instance, fraction 4 is quite good for AFB1 and Hg; fraction 8, 10, 15, 19 and 20 are active against AFB1 and very good for Hg; and fractions 12, 13, 14, 17 and 18 do not present AFB1 capture but are very good capturing Hg.

7.6. Bioavailability of the Fractions

Further to a detoxifying effect, the next point was to verify the suitability of these fractions for the desired use: to prevent the absorption of toxins present in food. To this end it was tested that they had a low bioavailability to be absorbed by the intestinal epithelium. The evaluation was done in Transwell plates with a method based in the differentiation of M cells in a model of Caco-2 cells by MIF (migration inhibitory factor) protein induction.

Preparation of the M Cells

Caco-2 cells were cultured on Transwell plates. Cells were growing during 14 days at 37° C., 5% $CO_2$ until total differentiation. The transephitelial resistance (TEER) was monitored during growing until a value of 250 $\Omega\cdot cm^2$ when MIF protein was added at a concentration of 0.3 μg/ml of supernatant. It was incubated for 5 h at 37° C. and 5% $CO_2$.

DTAF (Dichlorotriazinylaminofluorescein) Labeling of DAMM Product Fractions

The fractions were first milled until obtaining a fine powder. 20-25 mg of powder was diluted in 1 ml of borate buffer pH 9. The mixture was sonicated for 10 min at room temperature. Then, 1 ml DTAF 1 mg/ml was added and kept in constant agitation overnight. The final solution was centrifuged at 4000 rpm for 10 minutes with consecutive washings with 5 ml PBS. The different labeled fractions were added to the upper part of the Transwell plates and incubated for 3 h.

The determination was done with a fluorimeter mode well-scanning 520(Em)-490 (Ex). Dilutions 1/50 and 1/100 for each of the fractions were used. Analysis was made in duplicate deriving a mean value. In each case the % of penetration of the fraction in the model of intestinal epithelium was assessed. The results on bioavailability together with the previous capture results are shown in TABLE 14.

TABLE 14

| Fraction | Mean (%) bioavailability | Mean (%) capture |
|---|---|---|
| DAMM product | 7.20 | 19.3 |
| Fraction 2 (30 min 80° C. NaOH 50%) | 58.24 | 10.3 |
| Fraction 3 (120 min 80° C. NaOH 50%) | 55.02 | 16.3 |
| Fraction 5 (30 min 80° C. NaOH 25%) | 47.25 | 13.05 |
| Fraction 7 (240 min 80° C. NaOH 25%) | 51.07 | 12.5 |
| Fraction 9 (120 min 40° C. NaOH 50%) | 0.15 | 18.8 |
| Fraction 11 (30 min 40° C. NaOH 25%) | 62.53 | 15.42 |
| Fraction 12 (120 min 40° C. NaOH 25%) | 46.25 | 13.10 |

There is significant overlap between the fractions showing a greater capture and a less absorption, which is ideal for the detoxifying purposes.

Example 8

Immunostimulant Effect

A series of experiments were performed to determine the effect of the product on the immune system:

"Phage Test": quantitative determination of the phagocytic activity of monocytes and granulocytes in heparinized blood.
"Burst Test": determination of the oxidative activity of monocytes and granulocytes in heparinized blood.

Wistar rats were divided into two groups, each one of n=8; one with the experimental product and the other with a control. The experimental product was the fraction 2 of the previous section 7 obtained by hydrolysis for 30 minutes with 25% NaOH at 40° C. The assay took three weeks. Rats were kept at 12 h light/dark cycles with food and drink ad libitum. The feed basis was the same, and modified with the product to be tested:
 Control diet: standard rat diet (Teklad Global Diet, 2014);
 Experimental diet: standard rat diet (Teklad Global Diet, 2014) supplemented with 1.2 g of the experimental product. The immunostimulant dose was 100 mg experimental product/kg animal (30 mg/day)
During experimentation animal weight and feed consumed were monitored on a regular basis, together with values indicative of the state of the immune system in each of the groups. Sample collection was done on days 0 and 12 (total duration 22 days) by anesthetizing animals with isoflurane and removing a blood sample of the saphenous vein. The last day animals were anesthetized and sacrificed, obtaining the maximum volume of blood by cardiac puncture.

8.1. Phage Test

The Phage test allows determining the percentage of lymphocytes showing phagocytic capacity and the number of bacteria phagocytized by each lymphocyte that expresses the activity.

100 μl of blood were cooled to 0° C. in an ice bath and 20 μl of a cooled suspension of *Escherichia coli* fluorescently labeled was added. Samples were incubated at 37° C. in a water bath for 10 min. Then the samples were cooled. 100 μl of chelant solution were added to eliminate not internalized bacteria but adhered to the cell surface. 3 ml of buffer washing solution were added and the samples were centrifuged 5 min at 250 g at 4° C. The supernatant was disregarded and lysis buffer was added. The samples were incubated to eliminate non immune cells. 200 μl of DNA labeling solution were added to the obtained white cell fraction. After less than 1 h from labeling, cells were analyzed by flux cytometry. The DNA labeling of leukocyte cells, which emits fluorescence in the red range, allowed distinguishing the events (cells) which were leukocytes from the others. Using light refractive properties of each cell type, a histogram that allowed distinguishing neutrophils and monocytes was drawn. The results obtained by the Phage test are shown in TABLE 15.

TABLE 15

| | | Results of the Phage test | | | |
|---|---|---|---|---|---|
| | | Neutrophils | | Monocytes | |
| Day | Treatment | % boosted | Mean Fluorescence | % boosted | Mean Fluorescence |
| 12 | Control | 85.30 ± 0.96 | 93.20 ± 4.52 | 64.30 ± 3.31 | 59.07 ± 2.39 |
| | Experimental | 91.17 ± 4.52 | 133.23 ± 38.60 | 66.27 ± 6.93 | 76.47 ± 21.65 |
| 22 | Control | 96.34 ± 1.32 | 157.11 ± 29.31 | 65.54 ± 13.57 | 129.33 ± 18.75 a |
| | Experimental | 96.46 ± 1.05 | 183.11 ± 37.32 | 66.07 ± 9.97 | 162.44 ± 23.35 b |

Day 0 results were not available due to insufficient blood. Results are expressed as mean±S.D. for n=3 (blood samples were joined in a pool due to insufficient sample) on day 12 and n=9 at day 22. Samples from the same day and at the same column showing different letters show statistically significant differences (p<0.05).

It can be observed that the number of samples for day 12 was not large enough to establish statistically significant differences between treatments as regards number of cells. However, statistical significance is observed in the experimental group in increasing the mean fluorescence of neutrophils and monocytes in relation to the control sample. On day 22, there was no difference in the percentage of neutrophils and monocytes stimulated, i.e., the number of cells that were able to show phagocytic activity. With respect to monocytes, the experimental product significantly increased their activity in relation to the control group (p<0.01). Accordingly, the percentage of monocytes showing phagocytic capacity does not differ between treatments, but monocytes of those animals fed with experimental product show the ability to phagocyte or ingest a greater number of bacteria *E. coli* per stimulated monocytes.

8.2. Burst Test

The Burst test allows determining the ability of immune system cells to express oxidative activity, i.e. the potential to eliminate booster particles using oxygen-dependent mechanisms.

For each sample, 100 µl of blood were added into 3 different tubes, which were cooled in an ice bath at 0° C. 20 µl of buffer solution (negative control) were added to one of the 3 tubes while different boosters for the oxidative activity were added to the other tubes: E. *Coli* particles and ligand of protein kinase C-phorbol 13-myristate 12 acetate (PMA) as high control. The samples were mixed and incubated at 37° C. in a water bath 10 min. 20 µl of dehydrorodamine 123 substrate (DHR) which can be oxidized giving green fluorescence was added. It was incubated 10 min more. 2 ml of lysis solution were added and samples were incubated at 25° C. to eliminate erythrocytes. It was washed with buffer. 200 µl of DNA labeling solution were added to the obtained white cell fraction. After less than 1 h from labeling, cells were analyzed by flux cytometry. The sample size on days 0 and 12 was not large enough to determine statistically significant differences between treatments. Accordingly, the data analysis is focused primarily on the last day of treatment.

Based on the results, when high stimulation was used (PMA) no significant differences were observed in the activity of neutrophils. However, in the experimental group there was a tendency to increase the intensity of the fluorescence detected in monocytes, indicating a trend in increasing their activity. When the samples were subjected to a particulate stimulus (*E. coli*), animals fed with the experimental product showed a slight but no significant tendency to increase the percentage of neutrophils showing oxidative capacity. Referring to monocytes, the experimental group showed a higher percentage of cells showing oxidative capacity ($p<0.05$). Accordingly, as in the Phage test, the consumption of the experimental product works primarily increasing the response of monocytes. The results of the Burst test are shown in TABLE 16.

TABLE 16

Results of the Burst test, day 22, for *E. coli* particles

| Day | Treatment | Neutrophils | | Monocytes | |
|---|---|---|---|---|---|
| | | % boosted | Mean Fluorescence | % boosted | Mean Fluorescence |
| 22 | Control | 88.33 ± 5.48 | 6.06 ± 1.68 | 18.5 ± 7.4 | 3.37 ± 0.42 |
| | Experimental | 91.64 ± 4.19 | 6.1 ± 1.38 | 28.16 ± 7.6 | 3.59 ± 0.55 |

In conclusion, the experimental product had a significant effect in increasing the immune response. This activity was mainly focused on the ability of product to increase the response of monocytes against potential infectious process. Its intake implied a tendency to increase the phagocytic activity of neutrophils and a statistically significant increase in phagocytic activity of monocytes. It did not increase the proportion of leukocytes that express activity, but those that had expressed it had the ability to ingest a greater number of pathogens. The product increased the proportion of monocytes expressing oxidative activity when subjected to a particulate stimulus such as *E. coli*. Therefore, the product increased the amount of bacteria ingested by monocyte, which can enable a greater number of monocytes expressing oxidative activity. Extrapolation to human consumption to detect the same biofunctionalities would be with 5-6 grams daily.

Example 9

Industrial Scale-Up

Different batches of product were obtained by industrial process and were compared with that obtained as described in EXAMPLE 1 ("DAMM product" and referred herein as Batch 1).

For industrial scale-up, *Saccharomyces cerevisiae* by-product wet biomass resulting from brewing process was used as raw material.

9.1. Batch 2

The amount of dry material in the wet biomass was approximately 17% after drying the product at 105° C. From this 17%, a 13% corresponded to insoluble solids (*Saccharomyces cerevisiae* cells) and a 4% corresponded to soluble solids.

The reaction medium was prepared loading the reactor with 300 kg of distilled water, and adding 4 kg of NaOH. One-hundred kilograms of wet biomass were added to the reaction media which means that the ratio of wet biomass:reaction medium was of 1:3. Considering that the wet biomass contained 13% of yeast, the ratio would be 1:39 if expressed as dry yeast:reaction medium. The final concentration of NaOH was 0.25 M.

The mixture was heated until 80° C. and allowed to react with constant stirring at this temperature for 16 h. Once the reaction time elapsed, the product was chilled until room temperature. The mixture was centrifuged in order to separate the insoluble fraction in basic media by using a Gea Westfalia centrifuge (model SC 6-01-576, Hidrostop). Centrifugation was conducted by using flow-rates ranging from 100 to 300 l/h. The resulting residue was re-suspended again with 370 l of distilled water and neutralized by adding 3 M HCl until pH=7.1. Subsequently, the mixture was centrifuged as described above. The residue was finally washed by adding 360 l of water and centrifuging. The product obtained was dried by spray-drying. For this purpose, an aqueous suspension was maintained in the spray-drier by adding 4.5 l of water and constantly stirring during the process. The inlet and outlet temperature were 180° C. and 93-94° C., respectively. The product resulting from this process was a fine powder, named herein Batch 2.

9.2. Batch 3

The product was obtained by following the process for Batch 2 with minor modifications. Specifically, after hydrolysis at 0.25 M NaOH at 80° C. for 16 h, the mixture was directly neutralized by adding 3 M HCl (without the first centrifugation of the reaction mixture). After neutralization, the mixture was centrifuged and the procedure followed as described above. Therefore, compared to Batch 2 the procedure allowed obviating one centrifugation step optimizing the industrial costs. The product resulting is named herein Batch 3.

9.3. Batch 4

The amount of dry material in the wet biomass was approximately 18%. From this 18%, a 11% corresponded to insoluble solids (*Saccharomyces cerevisiae* cells) and a 7% to soluble solids.

The product was obtained as described for Batch 3 with minor modifications. The reaction medium was prepared loading the reactor with 300 kg of distilled water, and adding 5.7 kg of NaOH. 143 kg of wet biomass were used instead of 100 kg. They were added to the reaction media which means that the ratio of wet biomass:reaction medium was of 1:2. Considering that the wet biomass contained 11% of yeast, the ratio would be 1:23 if expressed as dry yeast:reaction medium. The final concentration of the NaOH was 0.32 M. The hydrolysis time was reduced from 16 to 10 h. Therefore, compared to Batch 3 the procedure resulted in a reduction of hydrolysis time. The product resulting is named herein Batch 4.

9.4. Product Characterization

Dietary fiber was determined following the official method AOAC 991.43 (AOAC Official Method 991.43. Total, Soluble and Insoluble Dietary Fiber in foods. Enzymatic—Gravimetric Method, MES—TRIS Buffer). Simple sugars were quantified by HPLC with refractive index detector. The results are shown in TABLE 17.

TABLE 17

| | (% by dry weight) | | | | |
|---|---|---|---|---|---|
| Parameter | Batch 1 | Batch 2 | Batch 3 | Batch 4 | Method |
| Dietary fiber | 44.18% | 47.53% | 51.64% | 51.46% | AOAC 991.43 |
| Simple sugars | <0.5% | <0.5% | <0.5% | <0.5% | HPLC/RI |

Glucans were determined following the method with reference K-YBGL 07/11 using the kit from Megazyme, which is described hereinafter. The reagents used in this method were:

Bottle 1: exo-1,3-β-Glucanase (100 U/ml) plus β-Glucosidase (20 U/ml) suspension, 2.0 ml. 8 ml of 200 mM sodium acetate buffer (pH 5.0) were added to bottle 1 (i.e. diluting the contents of the vial to 10 ml). It was divided into appropriately sized aliquots and stored in polypropylene tubes at −20° C. and on ice during use.

Bottle 2: Amyloglucosidase (1630 U/ml) plus invertase (500 U/ml) solution in 50% v/v glycerol, 20 ml.

Bottle 3: GOPOD Reagent Buffer. Buffer (48 mL, pH 7.4), p-hydroxybenzoic acid and sodium azide (0.4% w/v). Contents of bottle 3 were diluted to 1.0 l with distilled or deionized water.

Bottle 4: GOPOD Reagent Enzymes. Glucose oxidase plus peroxidase and 4-aminoantipyrine. Contents of bottle 4 were dissolved in the diluted contents of bottle 3 (see the preceding reagent). This reagent mixture (GOPOD reagent) was then divided into aliquots of desired volume for storage.

Bottle 5: D-Glucose standard solution (5 ml, 1.00 mg/ml) in 0.2% w/v benzoic acid.

Bottle 6: Control yeast β-glucan preparation (~2 g, β-glucan content stated on the bottle label).

Measurement of Total Qlucan (α-Qlucan+β-Qlucan) Plus D-Glucose in Oliqosaccharides, Sucrose and Free D-Glucose (a) Solubilization and partial hydrolysis of total glucan: samples were milled to pass a 0.5 mm screen using a Retsch centrifugal mill. The milled sample (100 mg) was added to a 20×125 mm Fisher Brand culture tube. The tube was tapped to ensure that all of the sample fell to the bottom of the tube. 1.5 ml of concentrated HCl (37% v/v) were added to each tube, the tubes capped and stirred vigorously on a vortex mixer. The tubes were placed in a water bath at 30° C. for 45 min and stirred on a vortex mixer every 15 min (to ensure complete dissolution of the β-glucan). 10 ml of water were added to each tube, the tubes capped and stirred on a vortex. The caps were loosened and the tubes placed in a boiling water bath (~100° C.). After 5 min the caps were tightened and the incubation continued for 2 h. The tubes were cooled to room temperature, the caps carefully loosened and 10 ml of 2 N KOH added. The contents of each tube were quantitatively transferred to a 100 ml volumetric flask using 200 mM sodium acetate buffer (pH 5.0) to wash the tube, and to adjust the volume. It was mixed thoroughly by inversion. An aliquot of each suspension was centrifuged at 1500 g for 10 min.

(b) Measurement of total glucan plus D-glucose in sucrose and free D-glucose: 0.1 ml aliquots (in duplicate) of centrifuged extract were transferred to the bottom of glass test tubes (16×100 mm). 0.1 ml of the mixture of exo-1,3-β-glucanase (20 U/ml) plus β-glucosidase (4 U/ml) in 200 mM sodium acetate buffer (pH 5.0) was added to the bottom of each tube; the tubes were mixed on a vortex and incubated at 40° C. for 60 min. 3.0 ml of glucose oxidase/peroxidase mixture (GO-POD) were added to each tube and incubate at 40° C. for 20 min. Absorbance of all solutions was measured at 510 nm against the reagent blank.

Measurement of α-Qlucan Plus D-Qlucose in Sucrose and Free D-Qlucose

Milled sample (100 mg) was added to a 20×125 mm Fisher Brand culture tube. The tube was tapped to ensure that all of the sample fell to the bottom of the tube. A magnetic stirrer bar (5×15 mm) was added followed by 2 ml of 2 M KOH to each tube and the pellets were resuspended by stirring for approx 20 min in an ice/water bath over a magnetic stirrer. 8 ml of 1.2 M sodium acetate buffer (pH 3.8) were added to each tube with stirring. Immediately 0.2 ml of amyloglucosidase (1630 U/ml) plus invertase (500 U/ml) were added and well mixed and the tubes were placed in a water bath at 40° C. The tubes were incubated at 40° C. for 30 min with intermittent mixing on a vortex stirrer. The contents of each tube were quantitatively transferred to a 100 ml volumetric flask and adjusted to volume with water. It was well mixed and an aliquot of the solution was centrifuged at 1500 g for 10 min. 0.1 ml aliquots (in duplicate) of either the diluted or undiluted supernatants were transferred into glass test tubes, 0.1 ml of sodium acetate buffer (200 mM, pH 5.0) plus 3.0 ml of GOPOD reagent were added and incubated at 40° C. for 20 min. The absorbance of all solutions was measured at 510 nm against the reagent blank.

The reagent blank consisted of 0.2 ml of sodium acetate buffer (200 mM, pH 5.0)+3.0 ml glucose oxidase/peroxidase reagent. The D-glucose standard consisted of 0.1 ml D-glucose standard (1 mg/ml)+0.1 ml of sodium acetate buffer (200 mM, pH 5.0)+3.0 ml glucose oxidase/peroxidase reagent.

Calculations $$\text{Total Glucan } (\% \text{ w/w}) = \Delta E \times F \times 100/0.1 \times 1/1000 \times 100/W \times 162/180 = \Delta E \times F/W \times 90$$

$$\alpha\text{-Glucan } (\% \text{ w/w}) = \Delta E \times F \times 1000 \times 1/1000 \times 100/W \times 162/180 = \Delta E \times F/W \times 90 \text{ (final volume 100 ml)} = \Delta E \times F/W \times 9.27 \text{ (final volume 10.3 ml)}$$

β-Glucan=Total Glucan−α-Glucan where: ΔE=reaction absorbance−blank absorbance.

F=a factor to convert absorbance to μg of D-glucose=100 (μg of the D-glucose standard)/GOPOD absorbance for 100 μg of D-glucose standard.

100/0.1=volume correction factor; for total glucan (yeast), (0.1 mL out of 100 ml was analyzed).

1000=volume correction factor; for α-glucan (0.1 ml out of 100 ml was analyzed).

1/1000=conversion from μg to milligrams.

100/W=conversion back to 100 mg of sample (i.e. as % w/w).

W=weight of sample analyzed.

$162/180$=a factor to convert from free D-glucose, as determined, to anhydroglucose, as occurs in β-glucan The results are shown in TABLE 18. It should be noted that the enzymatic method can quantify glucose coming from other non-glucan oligosaccharides, although the result is given as % of total glucans.

TABLE 18

(% by dry weight)

| Parameter | Batch 1 | Batch 2 | Batch 3 | Batch 4 | Method |
|---|---|---|---|---|---|
| β-glucans (1-3, 1-6) | 22.77% | 29.32% | 31.66% | 34.68% | Enzymatic |
| α-glucans | 50.80% | 42.36% | 30.24% | 27.55% | Enzymatic |
| Total glucans | 73.57% | 71.68% | 61.90% | 62.23% | Enzymatic |

β-glucans (1-3, 1-6) are included within the category of "dietary fiber" because they are non-digestible polysaccharides. This category would also include chitin/chitosan, among others. α-glucans instead are digestible polysaccharides and thus they are not included in "dietary fiber". The amount of simple sugars is negligible in all batches. In Batch 3 where the product was neutralized prior to the first centrifugation, the content in β-glucans is maintained compared to Batch 2 but less α-glucans are extracted. This is not problematic since the product biofunctionality is attributed to dietary fiber including β-glucans and chitin/chitosan.

Elemental Composition (Average of 3 Replicates)
Batch 2: 0.27% N, 42.99% C, 6.67% H
Batch 3: 0.50% N, 43.79% C, 6.77% H
Batch 4: 0.75% N, 42.82% C, 6.83% H The values are the same order of those obtained throughout the different processes. 1 mg of sample was submitted to combustion at 1200° C. and analyzed with a microanalizer.

NMRs $^1$H-NMR spectra were made dissolving the samples in $D_2O$ at a concentration of 20 mg/ml and were acidified with 30 μl of DCI, to completely dissolve the samples. 5 μl of a solution of TMSP (20 mg/ml in $D_2O$) were added as internal reference (0 ppm). Spectra were performed at 70° C. to avoid the overlap between the water signal with H1 of chitosan signal. A Bruker Avance 600 MHz was used with the following conditions of analysis: zgpr (pulse of 90 with presaturation of the water signal), number of accumulations: 128; spectral width: 12 ppm; presaturation 2-4.

Figure 4:
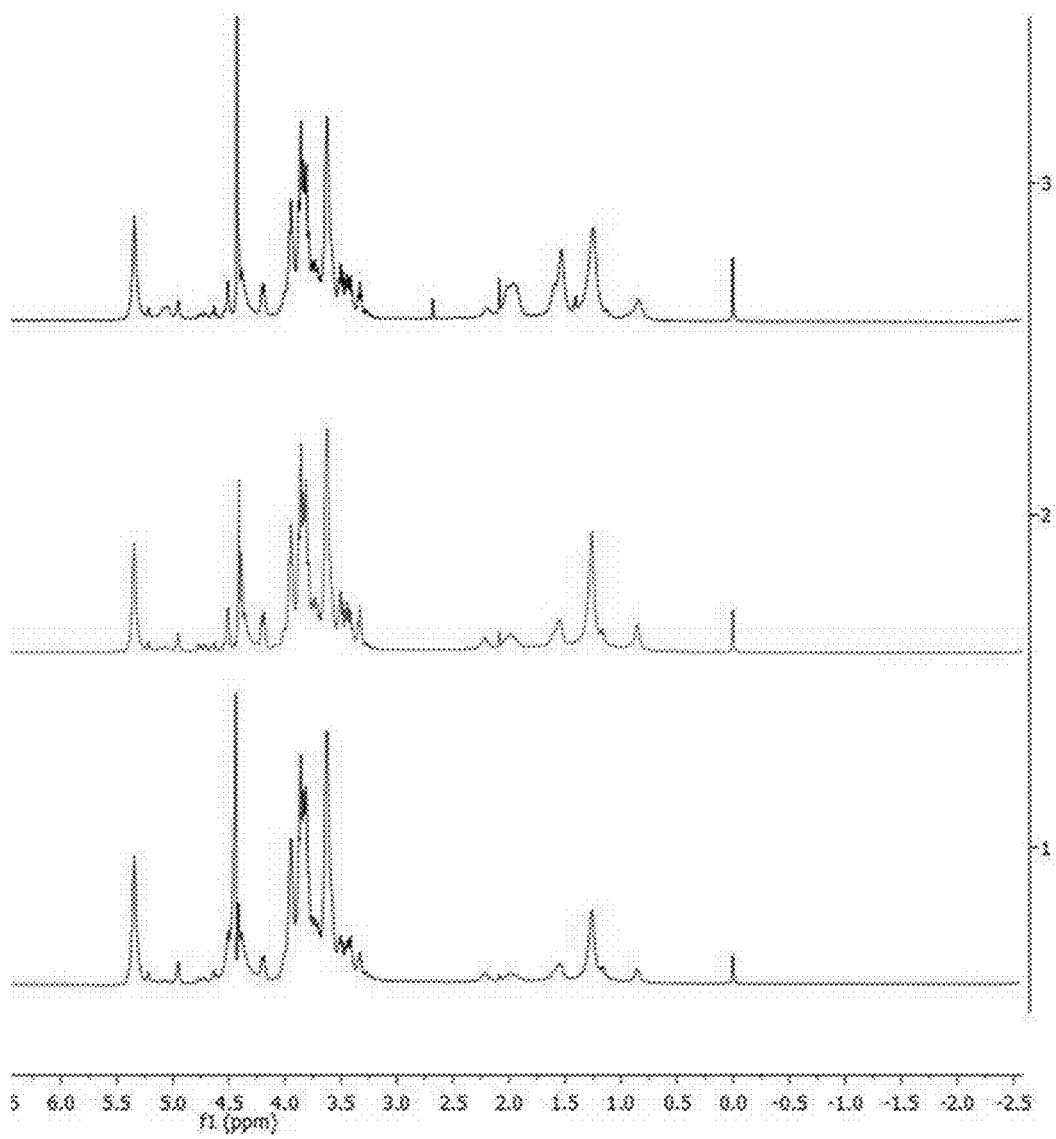
FIG. 4 shows the $^1$H-NMR analysis of products Batch 4 (upper figure), Batch 3 (middle figure) and Batch 2 (lower figure).

FIG. 4 shows the NMR spectra of Batch 2, 3 and 4. The region between 3.5-4 ppm shows all the peaks associated with the protons of polysaccharides (glucan, chitin, chitosan), which are the most intense in the spectra, since they are the major component of the product. The H1 of chitosan can be seen in all the spectra at around 5.3 ppm. The beta proton signal can be seen just before the water signal and alpha proton after the water signal. In this area of the spectrum, signals are very similar in intensity, so that the proportion of the different polysaccharides in the three batches should be very similar. At the same time, the spectra coincide with the NMR spectrum of the Batch 1 (FIG. 1).

REFERENCES CITED IN THE APPLICATION

N. Nwe et al. 2010, "Production of fungal chitosan by enzymatic method and applications in plant tissue culture and tissue engineering: 11 years of our progress, present situation and future prospects" *Biopolymers*, edited by Magdy Elnashar, published: Sep. 28, 2010, chapter 7 pp. 135-162

H. Yao et al., "Effect of chitosan on plasma lipids, hepatic lipids, and fecal bile acid in hamsters human trials failed to show these effects" *J. Food Drug Anal.* 2006, vol. 14, pp. 183-189

M. D. Gades et al., "Chitosan supplementation and fat absorption in men and women" *J. Am. Diet. Assoc.* 2005, vol. 105, pp. 72-77

C. N. Mhurchu et al., "Effect of chitosan on weight loss in overweight and obese individuals: a systematic review of randomized controlled trials" *Obes. Rev.* 2005, vol. 6, pp. 35-42

K. Zhou et al., "In vitro binding of bile acids and triglycerides by selected chitosan preparations and their physico-chemical properties" *Food Science and Technology* 2006, vol. 39, pp. 1087-1092

EP1483299

WO 91/03495

U.S. Pat. No. 4,810,646

The invention claimed is:

1. A process to obtain a composition comprising beta-glucan, chitin and chitosan, extracted from the cell wall of *Saccharomyces cerevisiae* from by-product biomass resulting from a brewing process, comprising the following steps:
   i) preparing a reactor with a NaOH solution in a concentration between 0.25 and 3 M with agitation and a temperature between 50 and 95° C.;
   ii) adding the by-product biomass resulting from the brewing process to the solution;
   iii) maintaining the conditions for at least 1 hour;
   iv) chilling the solution to room temperature,
   v) neutralizing the solution by at least one addition of an acidic solution or of water, until reaching pH 7, wherein when more than one addition is made, a step of separation of the solid product from the solution is performed between additions;
   vi) separating the solid product obtained in step (v) from the solution;
   vii) when the neutralization in step (v) has been made by the addition of an acidic solution, submitting the solid product to at least one washing with water and separating the obtained solid product; and
   viii) drying the solid product to constant weight and micronizing.

2. The process according to claim 1, wherein the temperature in step (i) is between 65 and 85° C.

3. The process according to claim 2, wherein the temperature in step (i) is 80° C.

4. The process according to claim 1, wherein the NaOH solution is in a concentration between 0.25 and 1.5 M.

5. The process according to claim 1, wherein the biomass resulting from the brewing process is added to the reactor in an amount between 1:2 and 1:5.

6. The process according to claim 1, further comprising separating the solid product from the solution of step (iv) before the step (v) of neutralization.

7. The process according to claim 1, wherein step (viii) is performed by spray-drying the product until a solvent content lower than 5% by weight is achieved.

8. The process according to claim 1, further comprising a pre-treatment of the biomass resulting from the brewing process before adding the biomass to the NaOH solution, the pre-treatment comprising the following steps:
   (a) sieving the biomass in order to separate the *Saccharomyces cerevisiae* biomass from impurities of the brewing process;
   (b) drying the *Saccharomyces cerevisiae* biomass obtained in step (a); and
   (c) milling the *Saccharomyces cerevisiae* product obtained in step (b).

9. A composition obtainable by the process as defined in claim 1.

10. A pharmaceutical and/or veterinary product comprising an effective amount of the composition as defined in claim 9, together with appropriate amounts of pharmaceutically or veterinary acceptable excipients.

11. An edible product comprising an effective amount of the composition as defined in claim 9, together with appropriate amounts of other edible ingredients.

12. The edible product according to claim 11, which is a dietary supplement.

13. A method for treatment of a disorder selected from the group consisting of overweight, obesity, hypercholesterolemia, hypertriglyceridemia, blood hypertension and cardiovascular disorders, in an animal, comprising administering to said animal in need thereof an effective amount of the composition of claim 9.

\* \* \* \* \*